(12) United States Patent
Chevalier et al.

(10) Patent No.: US 12,303,169 B1
(45) Date of Patent: *May 20, 2025

(54) BONE ELONGATING DEVICES AND METHODS OF USE

(71) Applicant: NuVasive, Inc., San Diego, CA (US)

(72) Inventors: Eric Chevalier, Palaiseau (FR); William Mercier, Paris (FR)

(73) Assignee: Nuvasive, Inc., San Diego, CA (US)

( * ) Notice: Subject to any disclaimer, the term of this patent is extended or adjusted under 35 U.S.C. 154(b) by 20 days.

This patent is subject to a terminal disclaimer.

(21) Appl. No.: 18/218,703

(22) Filed: Jul. 6, 2023

Related U.S. Application Data

(63) Continuation of application No. 17/332,022, filed on May 27, 2021, now Pat. No. 11,737,787.

(51) Int. Cl.
| | |
|---|---|
| *A61B 17/70* | (2006.01) |
| *A61B 17/72* | (2006.01) |
| *G16H 20/40* | (2018.01) |
| *G16H 40/67* | (2018.01) |
| *A61B 17/00* | (2006.01) |
| *A61B 34/00* | (2016.01) |
| *A61B 90/00* | (2016.01) |

(52) U.S. Cl.
CPC ...... *A61B 17/7016* (2013.01); *A61B 17/7216* (2013.01); *G16H 20/40* (2018.01); *G16H 40/67* (2018.01); *A61B 2017/00221* (2013.01); *A61B 2017/00991* (2013.01); *A61B 34/73* (2016.02); *A61B 2090/064* (2016.02)

(58) Field of Classification Search
CPC .............. A61B 17/014; A61B 17/7016; A61B 17/7216; A61B 2017/00991

USPC ...................................... 606/57, 63, 105, 258
See application file for complete search history.

(56) References Cited

U.S. PATENT DOCUMENTS

| | | |
|---|---|---|
| 2,702,031 A | 2/1955 | Leslie |
| 3,111,945 A | 11/1963 | Von |

(Continued)

FOREIGN PATENT DOCUMENTS

| | | |
|---|---|---|
| CN | 1697630 A | 11/2005 |
| CN | 101040807 A | 9/2007 |

(Continued)

OTHER PUBLICATIONS

Abe et al., "Experimental external fixation combined with percutaneous discectomy in the management of scoliosis.", Spine, 1999, pp. 646-653, 24, No. 7.

(Continued)

*Primary Examiner* — Ellen C Hammond
*Assistant Examiner* — Christina Negrellirodriguez

(57) ABSTRACT

An implant includes: an inner rod having an outer surface; an outer rod in telescopic engagement with the inner rod, the outer rod having a threaded inner surface in axial slidable engagement with the outer surface of the inner rod; the inner rod and the outer rod each having an end configured for attachment to bone; a rotational actuator housed within the inner rod; and a lead screw in axial alignment with the rotational actuator and rotationally coupled thereto, the lead screw in threaded engagement with the threaded inner surface of the outer rod, whereby rotational motion of the actuator is converted into linear motion, resulting in telescopic changes in the overall axial length of the device.

20 Claims, 24 Drawing Sheets

(56) References Cited

U.S. PATENT DOCUMENTS

| | | |
|---|---|---|
| 3,372,476 A | 3/1968 | Richard |
| 3,377,576 A | 4/1968 | Edwin |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |

(56) References Cited

U.S. PATENT DOCUMENTS

| | | |
|---|---|---|
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,559,951 B2 | 7/2009 | DiSilvestro et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,382,756 B2 | 2/2013 | Pool et al. |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |

(56) References Cited

U.S. PATENT DOCUMENTS

| | | |
|---|---|---|
| 8,668,719 B2 | 3/2014 | Alamin et al. |
| 8,709,090 B2 | 4/2014 | Makower et al. |
| 8,734,488 B2 | 5/2014 | Pool et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van Den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,044,281 B2 | 6/2015 | Pool et al. |
| 9,060,810 B2 | 6/2015 | Kercher et al. |
| 9,078,703 B2 | 7/2015 | Arnin |
| 9,078,711 B2 | 7/2015 | Quick |
| 9,248,043 B2 | 2/2016 | Payne et al. |
| 9,282,997 B2 | 3/2016 | Hunziker ............ A61B 17/7216 |
| 9,445,720 B2 | 9/2016 | Janna et al. |
| 9,883,896 B2 | 2/2018 | Kim et al. |
| 9,931,138 B2 | 4/2018 | Lynch ................ A61B 17/7017 |
| 10,314,619 B2 | 6/2019 | Roschak et al. |
| 10,702,375 B2 | 7/2020 | Roholt et al. |
| 10,835,290 B2 | 11/2020 | Cheng et al. |
| 11,246,694 B2 | 2/2022 | Cheng |
| 11,357,547 B2 | 6/2022 | Roschak et al. |
| 11,737,787 B1 * | 8/2023 | Chevalier ............ G16H 40/67 606/258 |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0133219 A1 | 7/2004 | Forsell |
| 2004/0138725 A1 | 7/2004 | Forsell |
| 2004/0193266 A1 | 9/2004 | Meyer |
| 2005/0034705 A1 | 2/2005 | Mcclendon |
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0094302 A1 | 4/2010 | Pool et al. |

(56) References Cited

U.S. PATENT DOCUMENTS

| | | |
|---|---|---|
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0060336 A1* | 3/2011 | Pool ............... A61B 17/1725 606/62 |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2011/0319755 A1 | 12/2011 | Stein et al. |
| 2012/0004494 A1 | 1/2012 | Payne et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2013/0338714 A1 | 12/2013 | Chang et al. |
| 2014/0005788 A1 | 1/2014 | Haaja et al. |
| 2014/0025172 A1 | 1/2014 | Lucas et al. |
| 2014/0031870 A1 | 1/2014 | Chang et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0025587 A1 | 1/2015 | Kim et al. |
| 2015/0105782 A1 | 4/2015 | D'Lima et al. |
| 2015/0105824 A1 | 4/2015 | Moskowitz et al. |
| 2015/0250505 A1 | 9/2015 | Ross |
| 2016/0058483 A1 | 3/2016 | Stauch |
| 2016/0113683 A1 | 4/2016 | Cheng |
| 2017/0049489 A1 | 2/2017 | Pool |
| 2017/0172624 A1 | 6/2017 | Brunner et al. |
| 2017/0333080 A1 | 11/2017 | Roschak |
| 2019/0254712 A1 | 8/2019 | Roschak et al. |
| 2020/0187989 A1 | 6/2020 | Hunziker |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 12/2011 |
| JP | H0956736 | 3/1997 |
| JP | 2002500063 A | 1/2002 |
| WO | WO1998044858 A1 | 10/1998 |
| WO | WO1999051160 A1 | 10/1999 |
| WO | WO2001024697 A1 | 4/2001 |
| WO | WO2001045485 A3 | 6/2001 |
| WO | WO2001045487 A2 | 6/2001 |
| WO | WO2001067973 A2 | 9/2001 |
| WO | WO2001078614 A1 | 10/2001 |
| WO | WO2007013059 A3 | 2/2007 |
| WO | WO2007015239 A3 | 2/2007 |
| WO | WO2011116158 A3 | 9/2011 |
| WO | WO2013119528 A1 | 8/2013 |
| WO | WO2014040013 A1 | 3/2014 |
| WO | 2020055874 A1 | 3/2020 |
| WO | 2020069627 A1 | 4/2020 |
| WO | 2020/163800 A1 | 8/2020 |
| WO | 2022/015898 A1 | 1/2022 |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi-Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", Sages Annual Scientific Sessions: Emerging Technology Poster Abstracts, 2007, ETP007, pp. 323-324.

(56) References Cited

OTHER PUBLICATIONS

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

Daniels et al., "A new method for continuous intraoperative measurement of Harrington rod loading patterns.", Annals of Biomedical Engineering, 1984, pp. 233-246, 12, No. 3.

De Giorgi et al., "Cotrel-Dubousset instrumentation for the treatment of severe scoliosis.", European Spine Journal, 1999, pp. 8-15, No. 1.

Dorsey et al., "The stability of three commercially available implants used in medial opening wedge high tibial osteotomy.", Journal of Knee Surgery, 2006, pp. 95-98, 19, No. 2.

Edeland et al., "Instrumentation for distraction by limited surgery in scoliosis treatment.", Journal of Biomedical Engineering, 1981, pp. 143-146, 3, No. 2.

Elsebaie, "Single growing rods (Review of 21 cases). Changing the foundations: Does it affect the results?", Journal of Child Orthop, 2007, 1:258.

Ember et al., "Distraction forces required during growth rod lengthening.", J of Bone Joint Surg BR, 2006, p. 229, 88-B, No. Suppl. II.

European Patent Office, "Observations by a third party under Article 115 EPC in EP08805612 by Soubeiran.", 2010.

Fabry et al., "A technique for prevention of port complications after laparoscopic adjustable silicone gastric banding.", Obesity Surgery, 2002, pp. 285-288, 12, No. 2.

Fried et al., "In vivo measurements of different gastric band pressures towards the gastric wall at the stoma region.", Obesity Surgery, 2004, p. 914, 14, No. 7.

Gao et al., CHD7 gene polymorphisms are associated with susceptibility to idiopathic scoliosis, American Journal of Human Genetics, 2007, pp. 957-965, 80.

Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).

Gillespie et al. "Harrington instrumentation without fusion.", J Bone Joint Surg Br, 1981, p. 461, 63-B, No. 3.

Goodship et al., "Strain rate and timing of stimulation in mechanical modulation of fracture healing.", Clinical Orthopaedics and Related Research, 1998, pp. S105-S115, No. 355S.

Grass et al., "Intermittent distracting rod for correction of high neurologic risk congenital scoliosis.", Spine, 1997, pp. 1922-1927, 22, No. 16.

Gray, "Gray's anatomy of the human body.", http://education.yahoo.com/reference/gray/subjects/subject/128, published Jul. 1, 2007.

Grimer et al. "Non-invasive extendable endoprostheses for children—Expensive but worth it!", International Society of Limb Salvage 14th International Symposium on Limb Salvage, 2007.

Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.

Guichet et al. "Gradual femoral lengthening with the Albizzia intramedullary nail", J Bone Joint Surg Am, 2003, pp. 838-848, 85-A, No. 5.

Gupta et al., "Non-invasive distal femoral expandable endoprosthesis for limb-salvage surgery in paediatric tumours.", J Bone Joint Surg Br, 2006, pp. 649-654, 88-B, No. 5.

Hankemeier et al., "Limb lengthening with the Intramedullary Skeletal Kinetic Distractor (ISKD).", Oper Orthop Traumatol, 2005, pp. 79-101, 17, No. 1.

Harrington, "Treatment of scoliosis. Correction and internal fixation by spine instrumentation.", J Bone Joint Surg Am, 1962, pp. 591-610, 44-A, No. 4.

Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.

Hofmeister et al., "Callus distraction with the Albizzia nail.", Practice of Intramedullary Locked Nails, 2006, pp. 211-215.

Horbach et al., "First experiences with the routine use of the Rapid Port™ system with the Lap-Band®.", Obesity Surgery, 2006, p. 418, 16, No. 4.

Hyodo et al., "Bone transport using intramedullary fixation and a single flexible traction cable.", Clinical Orthopaedics and Related Research, 1996, pp. 256-268, 325.

International Commission on Non-Ionizing Radiation Protection, "Guidelines on limits of exposure to static magnetic fields." Health Physics, 2009, pp. 504-514, 96, No. 4.

INVIS®/Lamello Catalog, 2006, Article No. 68906A001 GB.

Kasliwal et al., "Management of high-grade spondylolisthesis.", Neurosurgery Clinics of North America, 2013, pp. 275-291, 24, No. 2.

Kenawey et al., "Leg lengthening using intramedullay skeletal kinetic distractor: Results of 57 consecutive applications.", Injury, 2011, pp. 150-155, 42, No. 2.

Kent et al., "Assessment and correction of femoral malrotation following intramedullary nailing of the femur.", Acta Orthop Belg, 2010, pp. 580-584, 76, No. 5.

Klemme et al., "Spinal instrumentation without fusion for progressive scoliosis in young children", Journal of Pediatric Orthopaedics. 1997, pp. 734-742, 17, No. 6.

Korenkov et al., "Port function after laparoscopic adjustable gastric banding for morbid obesity.", Surgical Endoscopy, 2003, pp. 1068-1071, 17, No. 7.

Krieg et al., "Leg lengthening with a motorized nail in adolescents.", Clinical Orthopaedics and Related Research, 2008, pp. 189-197, 466, No. 1.

Kucukkaya et al., "The new intramedullary cable bone transport technique.", Journal of Orthopaedic Trauma, 2009, pp. 531-536, 23, No. 7.

Lechner et al., "In vivo band manometry: A new method in band adjustment", Obesity Surgery, 2005, p. 935, 15, No. 7.

Lechner et al., "Intra-band manometry for band adjustments: The basics", Obesity Surgery, 2006, pp. 417-418, 16, No. 4.

Li et al., "Bone transport over an intramedullary nail: A case report with histologic examination of the regenerated segment.", Injury, 1999, pp. 525-534, 30, No. 8.

Lonner, "Emerging minimally invasive technologies for the management of scoliosis.", Orthopedic Clinics of North America, 2007, pp. 431-440, 38, No. 3.

Matthews et al., "Magnetically adjustable intraocular lens.", Journal of Cataract and Refractive Surgery, 2003, pp. 2211-2216, 29, No. 11.

Micromotion, "Micro Drive Engineering. General catalogue.", 2009, pp. 14-24.

(56) References Cited

OTHER PUBLICATIONS

Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work?.", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", Spine, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", Sages Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "Veptr II. Vertical Expandable Prosthetic Titanium Rib II: Technique Guide.", 2008, 40 pgs.
Synthes Spine, "Veptr Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (Phenix®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", Spine, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.
Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.
Zheng et al., "Force and torque characteristics for magnetically driven blood pump.", Journal of Magnetism and Magnetic Materials, 2002, pp. 292-302, 241, No. 2.
International Search Report and Written Opinion for application No. PCT/US2022/054908 dated Dec. 19, 2022, 19 pages.

* cited by examiner

BONE ELONGATING DEVICES AND METHODS OF USE

PRIORITY CLAIM

This application is a continuation of, and claims priority to, co-pending U.S. patent application Ser. No. 17/332,022, filed on May 27, 2021, the entire contents of which are hereby incorporated by reference as a part of this application.

BACKGROUND

1. Field of the Invention

The present invention relates generally to bone elongation devices, and more particularly to compact bone elongation devices and methods for use in lengthening a bone, and for scoliosis correction, in a pediatric patient.

2. Description of the Background Art

Distraction osteogenesis is a surgical technique for lengthening a bone. Distraction osteogenesis consists of a controlled osteotomy followed by gradual and controlled distraction of the two bone ends utilizing a mechanical device which applies a stretching force to stimulate new bone growth. During the distraction phase, a distraction device causes distraction of the two bone segments starts at a specific rate and rhythm, typically at 1.0 mm per day.

Various distraction devices are known in the art. U.S. Patent Application Publication No. 2016/0058483 (Stauch), discloses a medullary pin for lengthening tubular bone comprising a hollow body containing axially displaceable first and second inner parts and a drive unit for generating axial displacement of the first inner part relative to the second inner part. An electrical cable provides power to the drive unit and allows for transmission of sensor signals from the device. U.S. Patent Application Publication No. 2011/0060336 (Pool) discloses an intramedullary lengthening device having an actuator with a housing containing a rotatable permanent magnet actuator and a movable distraction shaft telescopically mounted relative to the housing, wherein the distraction shaft is operatively coupled to the rotatable permanent magnet via a lead screw. U.S. Patent Application Publication No. 2017/0333080 (Roschak) discloses a remotely adjustable interactive bone reshaping implant including an implant body, an actuator coupled to the implant body, a sensor configured to detect a parameter indicative of a biological condition, a transceiver, and a controller.

Early onset scoliosis ("EOS") presents another bone-related issue wherein a deformity of the spine, particularly affecting children before the age of complete lung maturation, i.e. between 8-10 years of age. The management of EOS remains challenging since therapeutic approaches are largely directed to reducing and controlling the spinal curvature while maintaining and allowing for growth of the spine and thorax. Growing rods are one a popular treatment option for EOS because they can prevent curve deterioration while allowing spinal growth. Traditionally, growing rods require open manual distractions approximately every 6 months. These open manual distractions are burdened by increased risk of anesthetic and wound complications. Repeated surgery under general anesthesia also has potential deleterious effects on brain development. This is especially important for young children. As a result of the disadvantages associated with traditional growing rods (TGR's), the background art reveals the development of alternative technologies.

The published application to Chang et al. (US 2014/0031870), discloses a magnetically controlled growing rod ("MCGR") to allow for gradual lengthening on an outpatient basis. The MCGR allows for periodical noninvasive spinal lengthening under continuous neurological observation in an awake patient by use of a large external magnet. The published application to Kiester (US 2006/0009767) discloses correction of a scoliotic curve in a spine using an expanding rod isolated completely under the skin and attached to selected portions of scoliotic curve of the spine at opposite ends of the rod; and producing a controlled force by means of expansion of the rod over at an extended time period under external control until a desire spinal curve is obtained. The published application to Ross (US 2015/0250505) discloses a remotely controllable growing rod device containing on-board electronics with a microprocessor configured to receive remotely transmitted movement data through the receiver and further for feedback-controlled actuation of the drive assembly.

Unlike TGRs, the above-referenced technologies can be distracted during outpatient clinic visits, thereby avoiding the risks of repeated surgical lengthening. There is also the possibility for distractions to be carried out more frequently to mimic normal physiological growth more closely. This presents huge benefit for children as rod distractions no longer need to be carried out under general anesthesia. This may provide additional advantages to spine length gains by avoiding spine auto-fusion associated with sudden and forceful surgical distractions at irregular intervals. There remains, however, a need for further advancement in the art for device miniaturization, personalized protocols, and post-operative care follow-up.

While the various devices known in the art are generally suited for the specific uses for which they are intended, they are generally considered too large for use in treating pediatric cases. Further, the designs and mechanism used by the devices in the background art are generally not suitable for miniaturization to accommodate the smaller dimensions of pediatric bones without significant reductions in stroke length. In particular, the bone lengthening devices of the prior art relying on mechanical actuation wherein the actuator is configured in series with the distraction rod in a configuration wherein the length of the device is excessive. Accordingly, there exists a need for advancements in the field of bone lengthening to effectively treat pediatric cases.

Any art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. § 1.56 (a) exists.

BRIEF SUMMARY

The present invention overcomes the limitations present in the background art by providing advancements in the field of bone elongating devices and methods specifically adapted for use in lengthening the bones of pediatric subjects and treatment of pediatric scoliosis. In accordance with a first embodiment, the present invention provides an implantable bone elongation device including an outer rod and an inner rod configured in threaded telescopic engagement. The inner rod defines an internal cavity housing a rotational actuator having an output shaft connected to a lead screw disposed at the end of the inner rod and in threaded engagement with the threaded inner surface of the outer rod. Rotation of the lead screw converts rotation motion into linear motion resulting in telescopic movement of the outer rod relative to the inner rod. An aspect of the present invention is providing a configuration wherein the components that ensure and convert rotational motion into linear motion, namely an actuator and lead screw assembly on the one hand and an outer rod on the other hand, are positioned in a parallel configuration thereby minimizing the overall length of the bone elongating device while maintaining a maximum stroke length. In various embodiments additional components, such as electronic circuit boards, and an electrical power supply or battery power source, may be housed within the internal cavity formed by the inner rod. The bone elongation device of the present invention may be affixed to a bone in a variety of configurations including implantation into a medullary cavity of the bone, attached to an outer surface of the bone, or attached to the bone as an extramedullary plate.

Particular implementations include an implant having: an inner rod having an outer surface; an outer rod in telescopic engagement with the inner rod, the outer rod having a threaded inner surface in axial slidable engagement with the outer surface of the inner rod; the inner rod and the outer rod each having an end configured for attachment to bone; a rotational actuator housed within the inner rod; and a lead screw in axial alignment with the rotational actuator and rotationally coupled thereto, the lead screw in threaded engagement with the threaded inner surface of the outer rod, whereby rotational motion of the actuator is converted into linear motion, resulting in telescopic changes in the overall axial length of the device.

Further particular implementations include an implant having: an inner rod defining an internal volume; an outer rod in telescopically adjustable engagement with the inner rod, the outer rod defining an internal cavity bounded by a threaded inner surface; the inner rod and the outer rod each having an end configured for attachment to bone; an electronics package disposed within the internal volume; a rotational actuator in electrical communication with the electronics package; the rotational actuator including a motor and a gear assembly; a lead screw coupled to the gear assembly output, the lead screw having a threaded external surface disposed in threaded engagement with the threaded inner surface of the outer rod; and an implantable remote power module in electrical communication with the electronics package via a cable.

In certain cases, the rotational actuator comprises a non-electric actuator activated by an externally generated magnetic field.

In particular aspects, the inner rod further includes an externally disposed sleeve extending from an end portion thereof.

In some implementations, the implant further includes a sleeve extending from an end portion of inner rod over the outer rod configured to cover a gap that forms between the end portion and the outer rod as the axial length of the device increases.

In certain cases, the implant further includes a seal disposed adjacent to lead screw between an output shaft of rotational actuator and the inner rod.

In particular implementations, the inner surface of outer rod defines one or more radially inwardly projecting and longitudinally extending channels; and the outer surface of the inner rod defines one or more radially outwardly projecting and longitudinally extending lugs that are disposed within the channels.

In some aspects, the implant further includes an electronics package housed within the inner rod.

In particular cases, the implant further includes a force sensor configured to detect axial force applied to the device.

In certain cases, the rotational actuator comprises an electric motor.

In some implementations, the implant further includes an implantable remote power module in electrical communication with the electronics package via a cable.

Accordingly, it is an object of the present invention to provide advancements in the field of bone elongating devices and methods.

It is another object of the present invention to provide an improved bone elongating device specifically configured for use in lengthening the bone of a pediatric patient.

Still another object of the present invention is to provide a bone elongating device wherein the mechanical structures for ensuring and converting rotational motion to linear motion are configured in parallel thereby minimizing overall retracted length while maintaining a maximum stroke length.

Yet another object of the present invention is to provide advancements in the art of treating early onset scoliosis.

These and other objects are met by the present invention which will become more apparent from the accompanying drawing and the following detailed description of the drawings and preferred embodiments.

DETAILED DESCRIPTION

The present invention may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

In describing this invention, the word "coupled" is used. By "coupled" is meant that the article or structure referred to is joined, either directly, or indirectly, to another article or structure. By "indirectly joined" is meant that there may be an intervening article or structure imposed between the two articles which are "coupled". "Directly joined" means that the two articles or structures are in contact with one another or are essentially continuous with one another. By adjacent to a structure is meant that the location is near the identified structure.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
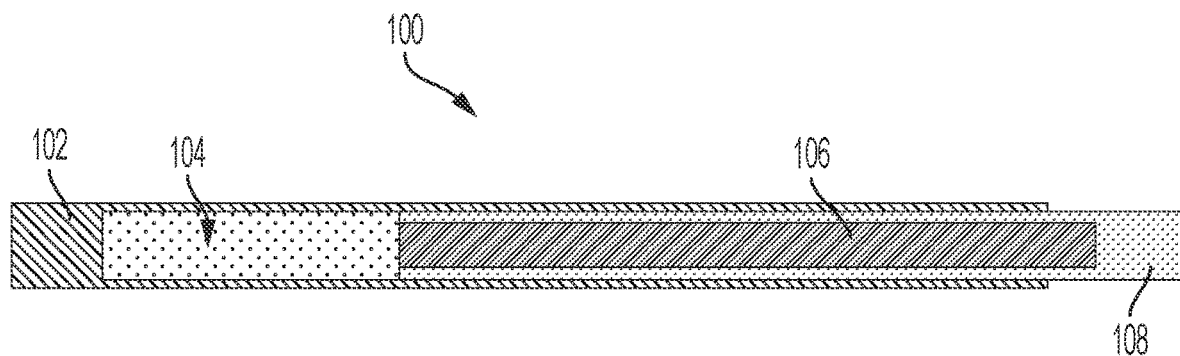
FIG. 1 is a schematic cross-sectional illustration of a prior art bone elongating device having an actuator and lead screw assembly in threaded engagement with an inner rod, in series, to ensure and translate rotational motion into linear motion.

Turning now to the drawings, FIG. 1 is a schematic illustration of a bone lengthening device, generally referenced as 100, in accordance with the prior art wherein the components for translating rotational motion into linear motion are configured in series as further discussed hereinbelow. FIG. 1 depicts the prior art device 100 in a non-extended configuration. Prior art device 100 includes an outer rod 102 housing a rotational actuator 104 directly coupled in series to an externally threaded lead screw 106 which is in threaded engagement with an inner rod 108. Rotational actuation of lead screw 106 causes inner rod 108 to extend relative to outer rod 102. In the context of the present invention, the prior art configuration wherein the rotational actuator 104, lead screw 106, and threaded inner rod 108 are arranged as seen in FIG. 1 shall be construed as a configuration with said components mechanically arranged in "series." As best seen in FIG. 1, the mechanical configuration wherein the rotational actuator 104 and lead screw 106 are fixedly housed in series within the outer rod 102 results in a device having an excessive overall length.

Figure 2:
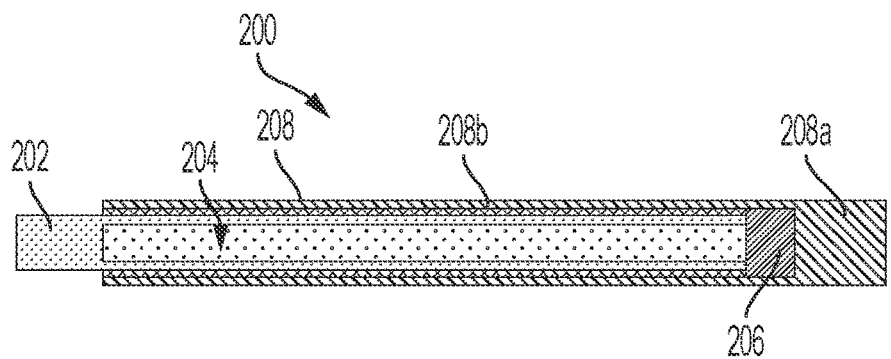
FIG. 2 is a schematic cross-sectional illustration of a bone elongating device in accordance with the present invention with an actuator and lead screw configured in parallel relative to an outer rod to ensure and translate rotational motion into linear motion.
Figure 3A:
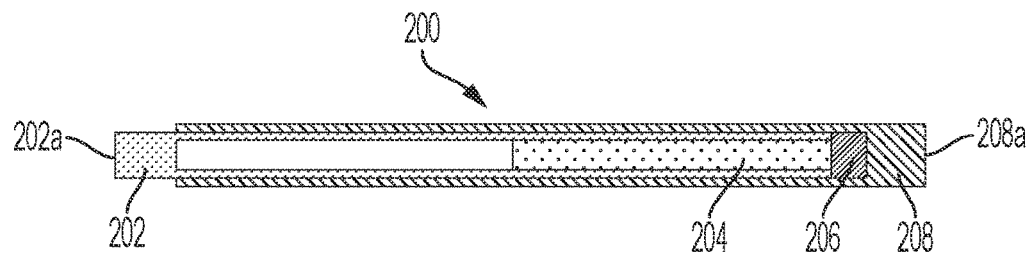
FIG. 3A is a schematic cross-sectional illustration of a bone elongating device in accordance with the present invention in a retracted configuration.
Figure 3B:
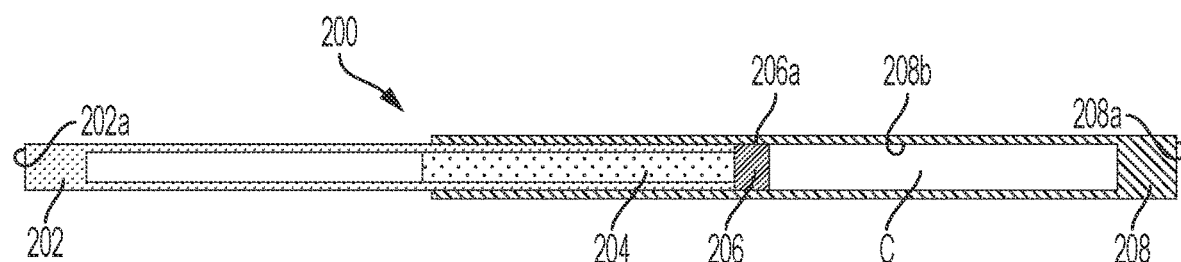
FIG. 3B is a schematic cross-sectional illustration in accordance with the device illustrated in FIG. 3A in a lengthened configuration.
Figure 3C:
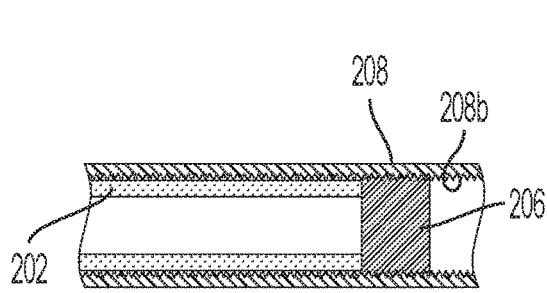
FIG. 3C is a partial schematic detailed view of the device illustrated in FIG. 3B.
Figure 3D:
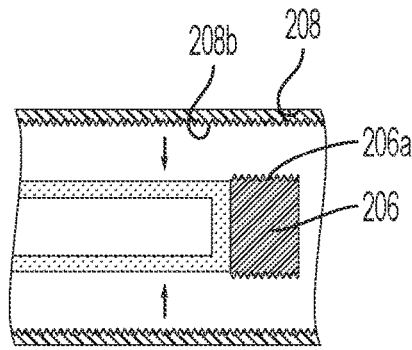
FIG. 3D is an exploded partial schematic detailed view of the device illustrated in FIG. 3C.

FIGS. 2-32 disclose various embodiments of an implantable bone lengthening/elongating device various methods of using same in accordance with the present invention. FIG. 2 provides a schematic illustration of a bone lengthening device, generally referenced as 200, in accordance with the present invention. More particularly, bone elongating device 200 includes an inner rod 202 housing a rotational actuator 204 configured to drive a lead screw 206 which in turn is in treaded engagement with an internally threaded surface 208b of an outer rod 208. As best seen in FIG. 2, the mechanics for translating and ensuring rotational motion into linear motion, namely the lead screw 206 and threaded inner surface 208b of outer rod 208, and outer rod 208 surrounding inner rod 202, are configured in "parallel" relative to rotational actuator 204, thereby resulting in significant reduction in overall length when compared with series configured devices known in the prior art. Inner rod 202 and outer rod 208 are preferably fabricated from surgical grade stainless steel. In some embodiments inner rod 202 and outer rod 208 may be tubular, however, in other contemplated embodiments inner rod 202 and outer rod 208 may be of different configurations provided that they are configured in a manner that allows for rotational motion to be converted to relative linear motion.

There are significant differences between bone lengthening devices configured in "parallel" vs. "series." Devices configured in series in accordance with the prior art have the rotational actuator disposed within the outer rod and driving a lead screw in threaded engagement with a threaded inner surface of the inner rod. In contrast, devices configured in parallel in accordance with the present invention have the rotational actuator disposed within the inner rod and configured to drive a lead screw in threaded engagement with a threaded inner surface of the outer rod. Housing the rotational actuator (as well as other components) in the inner tube results in a device having a more compact length as compared with prior art devices.

As best seen in FIGS. 3A, 3B, 3C, and 3D, an implantable bone lengthening device 200 in accordance with the present invention includes an inner rod 202 disposed in the inner cavity, referenced as "C" defined by an interior volume of outer rod 208. Inner rod 202 is telescopically disposed at least partially within an inner cavity C of the outer rod 208 and preferably includes an end portion 202a partially projecting from outer rod 208 which terminates at an opposing end 208a. Inner rod 202 is tubular and defines and internal volume housing at least a rotational actuator 204. A lead screw 206 is disposed at the opposite end of the inner rod 202 from end portion 202a and is rotationally coupled to rotational actuator 204. Lead screw 206 is generally cylindrical and defines a threaded outer peripheral surface 206a configured for threaded mating engagement with a threaded inner surface 208b of outer rod 208 which surrounds inner cavity C. The threads may be of any suitable shape and dimension; thread pitch, helical angle, thread angle, and crest/root dimension, so long as the threads of the lead screw 206 reliably engage with the threads 208b formed on the inner surface of outer rod 208. In some embodiments, the threads are metric iso triangular, (a portion of a metric iso triangular profile, a metric trapezoidal, a UTS profile). In some embodiments, the thread pitch is 0.4 mm, in other embodiments the tread pitch may differ, preferably falling within a range from 0.05 mm to 2.0 mm. Bone lengthening device preferably fabricated with an overall retracted length of 120.0 mm, and diameter of 8.0 mm, a stroke length of 50 mm, and capable of generating an axial force of 600 Newtons. As should be apparent, variations of those dimensions may be made without departing from the scope of the present invention.

Rotational actuator 204 drives lead screw 206 to rotate relative to inner rod 202. Outer rod 208 is restricted, as more fully discussed herein below, from rotating relative to inner rod 202 but is otherwise free to move axially along the length of the inner rod 202. Actuation of rotational actuator 204 causes the lead screw 206 to rotate thereby causing outer rod 208 to move axially relative to inner rod 202. Accordingly, selective actuation of rotational actuator 204 extends the length of implantable bone lengthening device 200 when the lead screw rotates in a first direction, and reduces the length of the implantable bone lengthening device 200 when the rotational actuator 204 causes screw 206 to rotate in the opposite direction.

In some embodiments, the rotational actuator 204 includes an electric motor configured to provide a rotational movement to the lead screw 206 upon activation by an electrical signal. In other embodiments, the rotational actuator 204 includes a cylindrical magnet (e.g. magnetically actuated motor) configured to generate rotational movement to the lead screw 206 upon activation by an externally generated magnetic field. Further, any suitable apparatus for generating rotational actuation of lead screw 206 is considered within the scope of the present invention.

Figure 4:
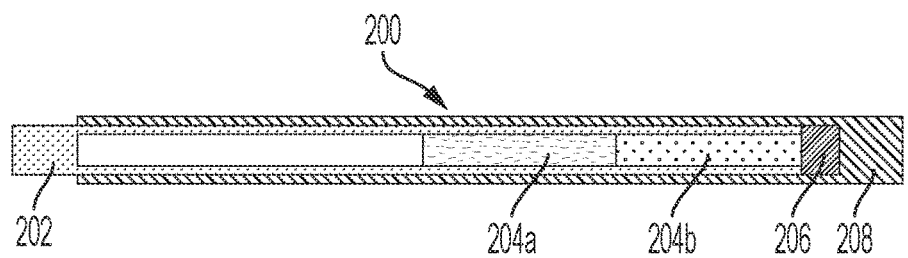
FIG. 4 is a schematic cross-sectional illustration of an alternate embodiment bone elongating device in accordance with the present invention configured with an electric motor and reducer.

As illustrated in FIG. 4, in some embodiments the rotational actuator 204 may comprise an electrical motor or a cylindrical magnet 204*a*, or any other suitable actuator apparatus. In addition, the actuator assembly may further include a reducer 204*b* coupling the motor or the magnet 204*a* to lead screw 206. Reducer 204*b* functions to increase the torque of the rotational actuator (e.g. a miniature motor) to a desired torque for driving lead screw 206 while maintaining an acceptable speed. In some embodiments, the reducer 204*b* includes a gear assembly or gear box, such as a planetary gearbox. In some embodiments, the reducer 204*b* includes a strain wave gear reducer. In some embodiments, the reducer 204*b* includes a hypocycloid reducer. In some embodiments, the reducer 204*b* includes any two of: planetary gearing, strain wave reducer, and/or hypocycloid reducer. In some embodiments, the reducer 204*b* includes all three of: planetary gearing, strain wave reducer, and hypocycloid reducer.

Figure 5:
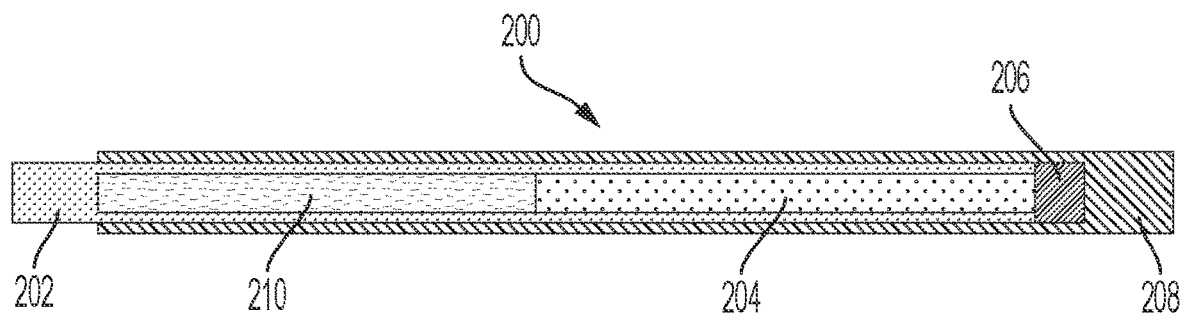
FIG. 5 is a schematic cross-sectional illustration of an alternate embodiment bone elongating device in accordance with the present invention configured with a rotational actuator and an electronic circuit.
Figure 6:
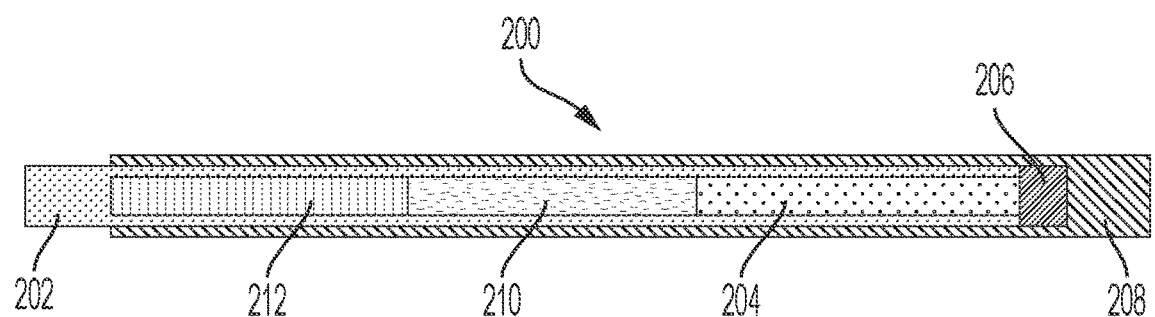
FIG. 6 is a schematic cross-sectional illustration of an alternate embodiment bone elongating device in accordance with the present invention configured with an internal power source.
Figure 7:
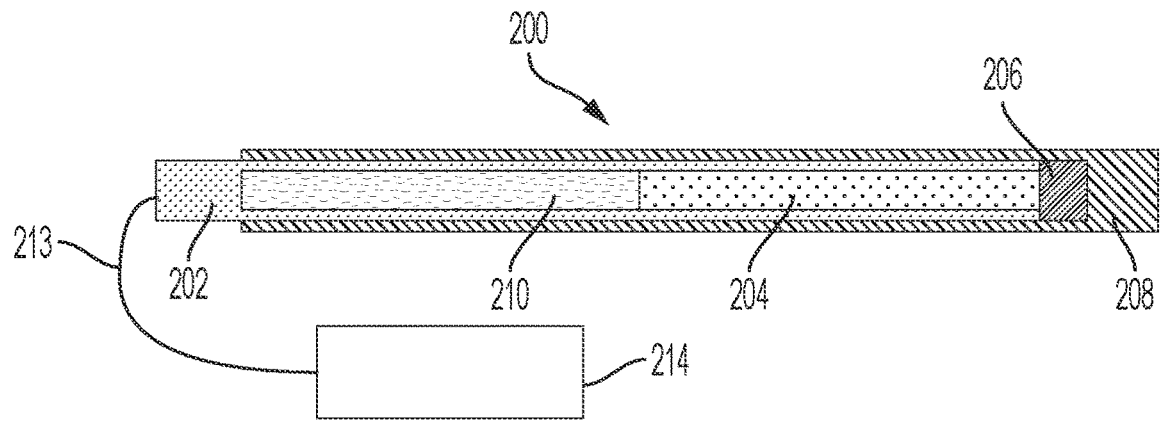
FIG. 7 is a schematic cross-sectional illustration of an alternate embodiment bone elongating device in accordance with the present invention configured with an implantable remote powering module.

As best seen in FIG. 5, inner rod 202 may further house an electronics package 210, such as powering electronics, sensors, motor drivers, controller. As further illustrated in FIG. 6, inner rod 202 may include a rotational actuator 204, an electronics package 210, and an electrical power source 212. Electrical power source 212 may include a battery, primary cell, a wireless power receiver, or any other suitable apparatus capable of receiving and/or delivering electrical power. In a contemplated alternate embodiment shown in FIG. 7, power may be supplied to the device, such as the electronics 210 housed within inner rod 202, via an electrically conducting cable 213 electrically connected to an implantable remote power module 214. Remote power module 214 may comprise an energy storage device such as a battery or a primary cell and may further optionally some electronics. In another contemplated embodiment implantable remote powering module 214 may comprise a wireless power receptor, and optionally some electronics.

Figure 8:
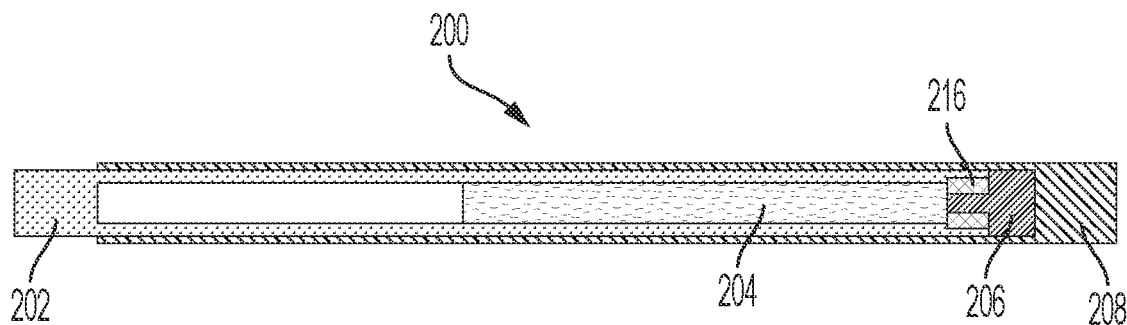
FIG. 8 is a schematic cross-sectional illustration of an alternate embodiment configured with a bearing.

With reference to FIG. 8, there is disclosed an embodiment of an implantable bone lengthening device 200 further including a bearing 216 capable of operation when exposed to axial and/or radial forces. Bearing 216 withstands forces applied between the inner rod 202 and lead screw 206 allows rotational movement of the lead screw 206 relative to the inner rod 204. Bearing 216 further transmits axial and/or radial forces applied to the outer rod 208 through lead screw 206 to the inner rod 202. Bearing 216 may comprise a thrust bearing, such as a thrust ball bearing, a thrust roller bearing, tapered roller bearing, a thrust needle bearing, or a thrust plain bearing. In other contemplated embodiments bearing 216 may comprise a radial bearing, such as a radial ball bearing, a radial roller bearing, a radial needle bearing or a radial plain bearing. In other contemplated embodiments bearing 216 is an angular contact bearing, such as an angular contact ball bearing, an angular contact conical roller bearing, or a plain angular contact bearing. In still other contemplated embodiments, bearing 216 may comprise a combination of more than one bearing, or a combination of more than one bearing and bearing type such as a combination of several axial, radial and angular contact bearings. Further bearing 216 may comprise a single row bearing, double row bearing, or bearing(s) designed for forces applied in one or more directions.

Figure 9A:
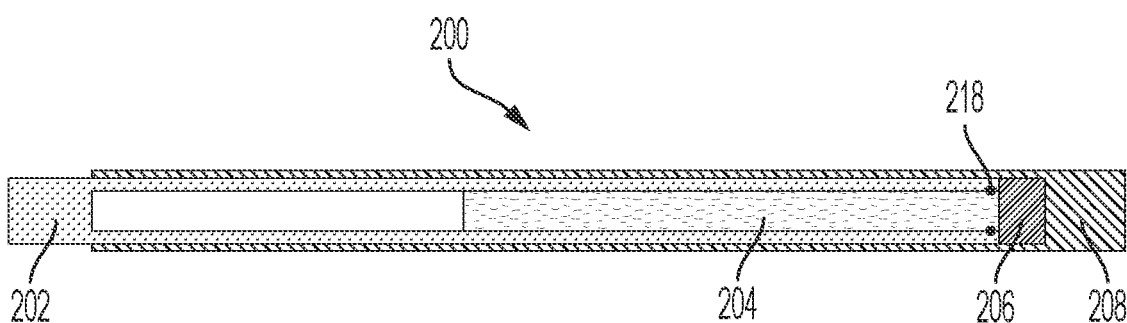
FIGS. 9A and 9B are schematic cross-sectional illustrations of alternate embodiments configured with various seals.
Figure 9B:
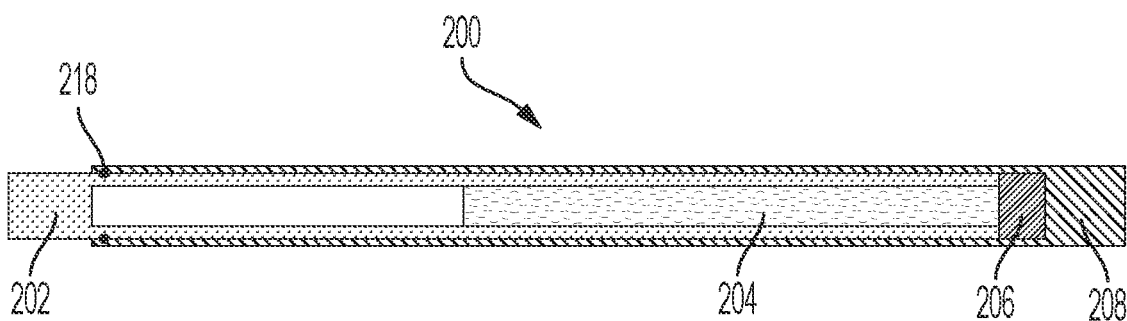

FIGS. 9A and 9B depict yet another embodiment adapted with a seal 218. Seal 18 functions to hermetically seal the device whereby biocompatible components which can be in direct contact with patient tissues are separated by seal 18 from non-biocompatible components which must be isolated from patient tissues. Seal 218 may be used in conjunction with one or more of the bearing configurations disclosed herein. FIG. 9A illustrate use of a seal 218 disposed adjacent to lead screw 206 between the output shaft of rotational actuator 204 and inner rod 202. FIG. 9B illustrates use of seal 218 disposed between the inner rod 202 and the outer rod 208 in proximity to the projecting end of inner rod 202. Seal 218 may comprise, consist essentially of, or consist of an O-ring. In other contemplated embodiments seal 218 comprises, consists essentially of, or consists of an X-ring. In yet other embodiments seal 218 comprises, consists essentially of, or consists of an O-ring, X-ring, V-ring, leap-seal or any other shape seal.

Figure 10:
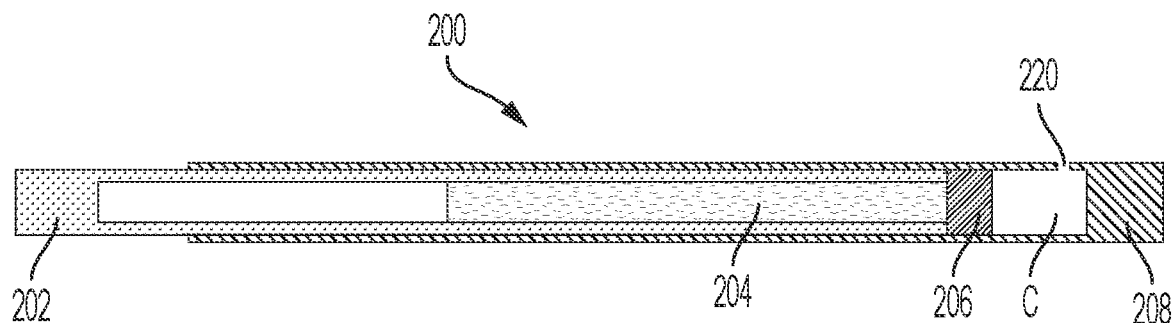
FIG. 10 is a schematic cross-sectional illustration of an alternate embodiment configured with a vent.
Figure 11:
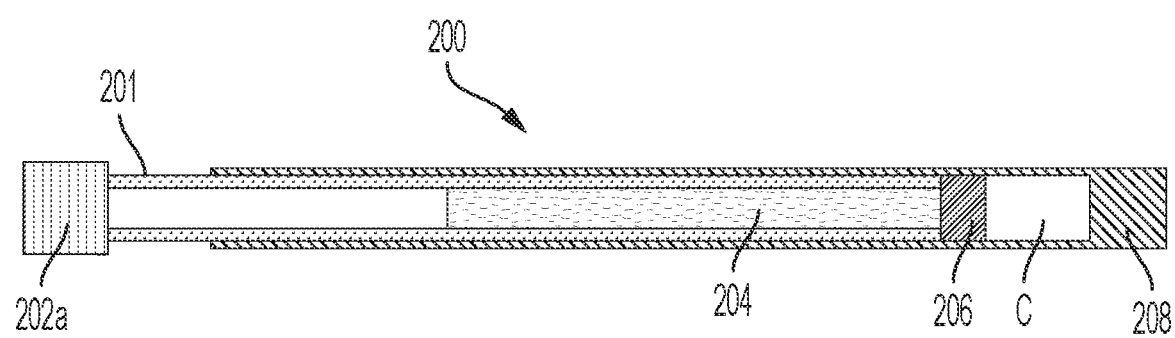
FIG. 11 is a schematic cross-sectional illustration of an alternate embodiment configured with a radially enlarged inner rod tip.
Figure 12A:
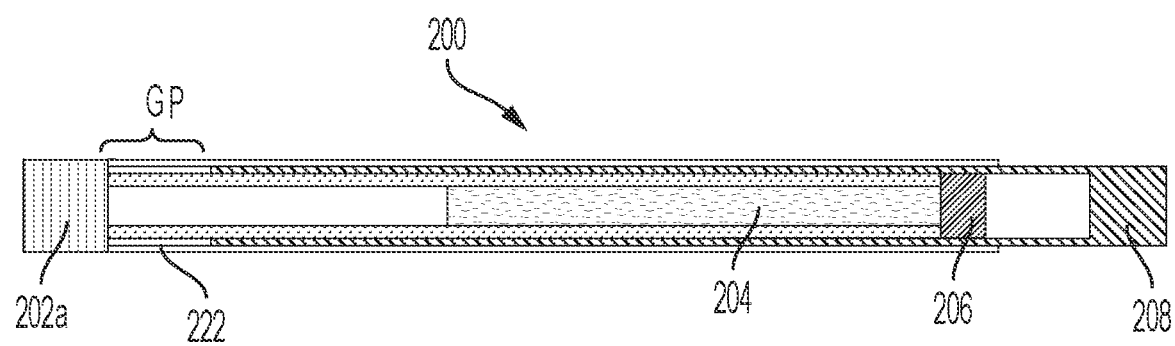
FIG. 12A is a schematic cross-sectional illustration of an alternate embodiment configured with a sheath in a fixed assembly with the inner rod and covering the outer rod.
Figure 12B:
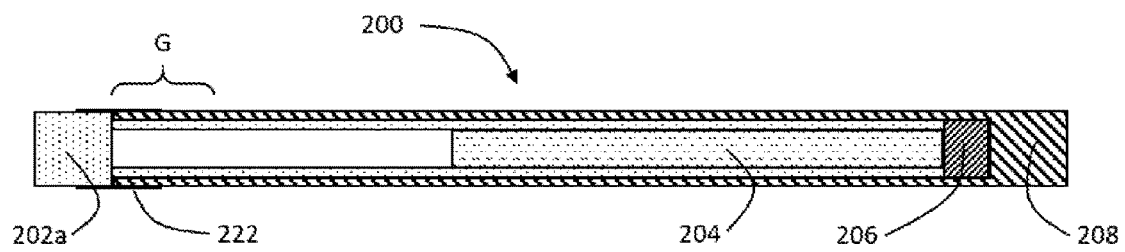
FIG. 12B is a schematic cross-sectional illustration of another alternate embodiment sheath configuration with the device in a retracted configuration.
Figure 12C:
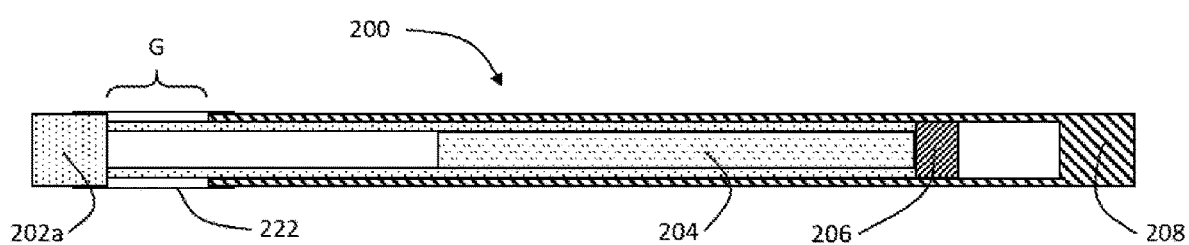
FIG. 12C is a schematic cross-sectional illustration of the embodiment shown in FIG. 12B but a partially extended configuration.

Referring now to FIG. 10, outer rod 208 may be adapted to include a vent 220 placing inner cavity C in fluid communication with the environment exterior to outer rod 208. Vent 220 operates to prevent a pressure differential (e.g., pressure reduction or vacuum) from forming across the wall of the outer rod 208 as the outer rod is advanced axially along the inner rod 202 as the inner cavity C expands. Vent 220 may further allow for cavity C to be filled with air or a gas at implantation. Vent 220 may be formed by a through bore or may further include fluid communication via channels formed in outer rod 208.

As illustrated in FIGS. 11 and 12A-12C, an implantable bone lengthening device may be configured wherein the projecting end portion 202*a* of inner rod 202 has an external diameter that is approximately the same as, is the same as, or is greater than the external diameter of outer rod 208. In those embodiments, a sleeve 222 may extend from the end portion 202*a* of inner rod 202 over the outer rod 208, to prevent growth of tissue in the gap G that forms between the end portion 202*a* and the outer rod 208 as the outer rod 208 moves axially along the inner rod 202 as shown in FIG. 12. Sleeve 222 may be fabricated from surgical grade steel, or any other suitable material, and the outer rod slides freely within the sleeve or sheath.

Figure 13:
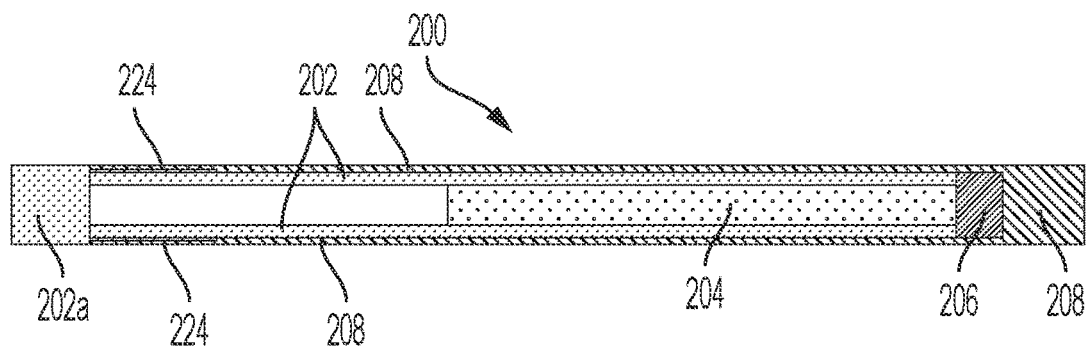
FIG. 13 is a schematic cross-sectional illustration of an alternate embodiment configured with a guide bushing.

In an embodiment shown in FIG. 13, a bushing 224 is disposed in outer rod 208 in proximity to the projecting end portion 202*a* of inner rod 202. Bushing 224 functions to ensure proper alignment of the inner rod 202 and the outer rod 208, and to reduce or minimize play between inner rod 202 and outer rod 208. In addition, bushing 224 functions to reduce friction between components to ensure smooth sliding of outer rod 208 on inner rod 202.

Figure 14:
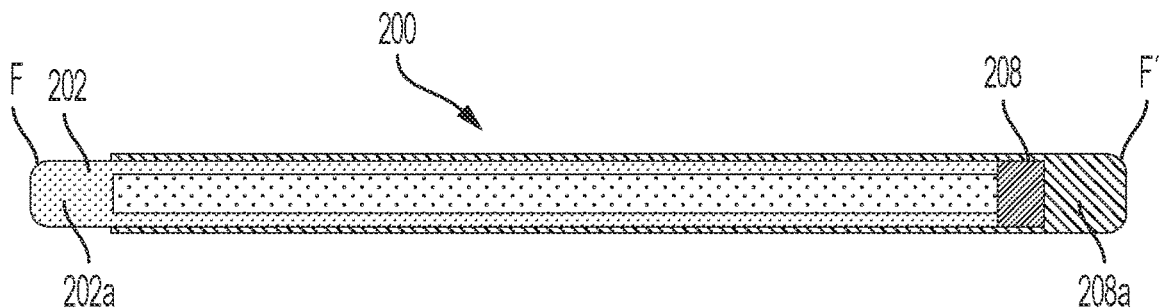
FIG. 14 is a schematic cross-sectional illustration of an alternate embodiment configured with fillet ends.

Referring now to FIG. 14, the projecting portion 202*a* of the inner rod 202 may include a filleted end profile F to reduce or minimize abrasion damage to tissue surrounding the implantable bone lengthening device 200. The end portion 208*a* of the outer rod 208 may also include a filleted end profile F' to reduce or minimize abrasion damage to tissue surrounding the implantable bone lengthening device 200.

Figure 15:
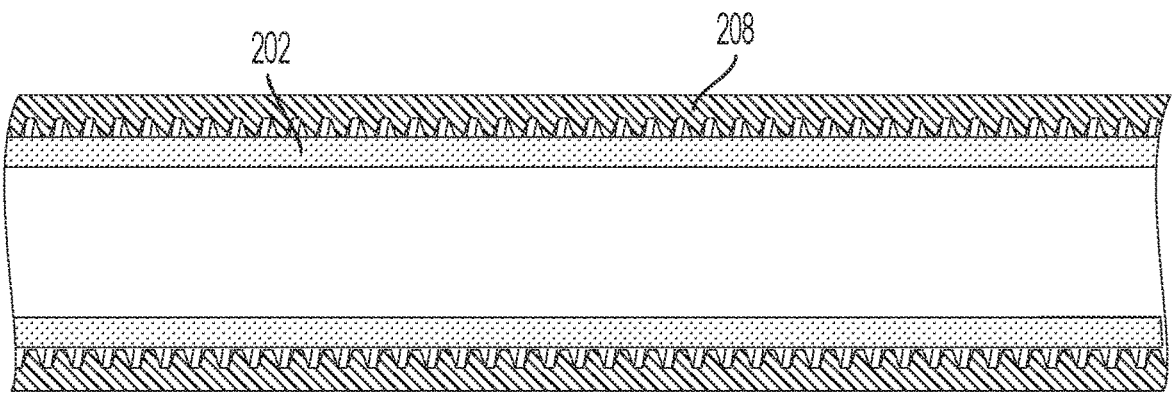
FIG. 15 is a partial cross-sectional detailed illustration providing a detailed depiction of structure that allows sliding engagement between the inner and outer rods.

FIG. 15 provides a detailed partial sectional view illustrating the sliding engagement between inner rod 202 and outer rod 208. The threads formed on the inner surface of the outer rod 208 are in sliding engagement with the generally smooth outer surface of the inner rod 202 in order to make outer rod 208 slide properly on inner rod 202. Inner rod 202 and outer rod 208 are formed with precise tolerances in order to maximize a balance between friction and play. In some embodiments, the lead screw 206 includes a metric iso triangular thread form. In some embodiment the outer rod 208 includes a portion of a metric iso triangular thread form.

Figure 16A:
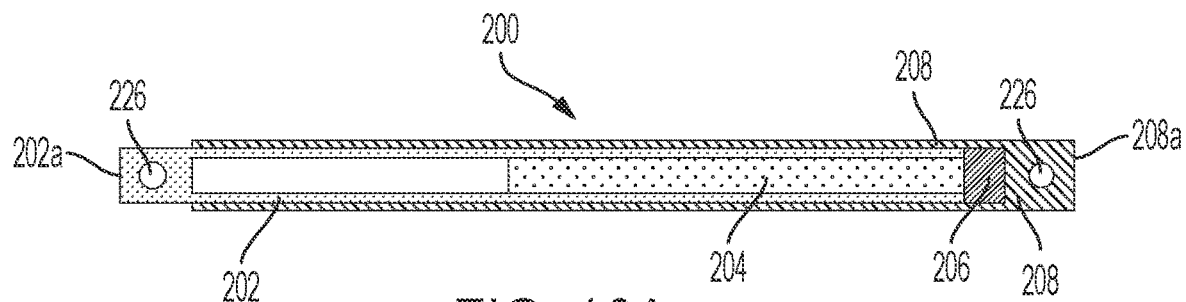
FIGS. 16A and 16B are schematic cross-sectional illustrations showing inner and outer rod ends adapted with fastener receiving apertures for use in attaching the device to a bone segment.
Figure 16B:
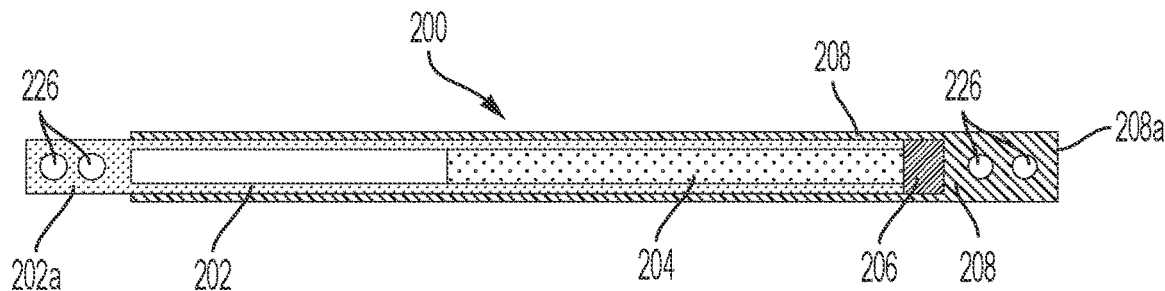
Figure 17:
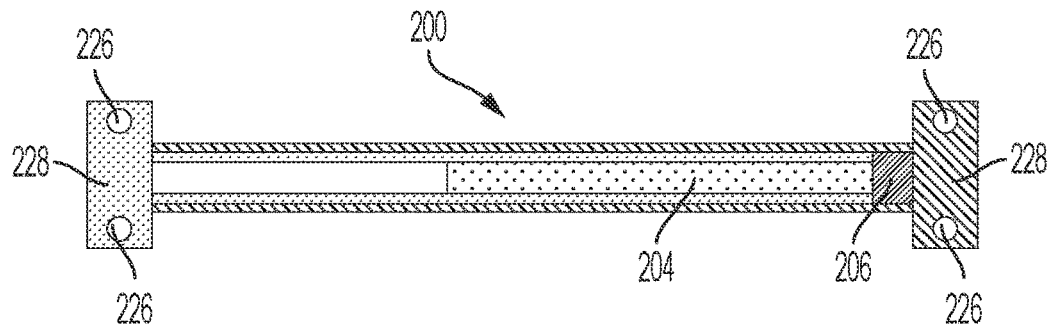
FIG. 17 is a schematic cross-sectional illustration depicting the device adapted with lateral fixation plates.

FIGS. 16A, 16B, and 17 depict embodiments of a bone lengthening device in accordance with the present invention adapted with opposing ends configured to facilitate attachment of the device to bone. With reference to FIG. 16A, bone lengthening device 200 includes the inner rod end portion 202*a* and the outer rod end portion 208*a* each define a through-bore 226 through which a bone screw or other suitable fastener or attachment device may be fed to attach the opposing ends of bone lengthening device 200 to corresponding sections of bone. FIG. 16B illustrates an alternate embodiment wherein the inner rod end portion 202*a* and the outer rod end portion 208*a* each define a pair of longitudinally aligned through-bores 226, each of which is intended to receive a bone screw or other suitable fastener or attachment device may be fed to attach the opposing ends of bone lengthening device 200 to corresponding sections of bone. FIG. 17 illustrates yet another embodiment wherein inner rod 202 and the outer rod 208 are adapted with lateral fixation plates 228, each of which define a pair of through bores 226. As should be apparent, inner rod 202 and the outer rod 208 may be configured with a variety of through-bore and fixation plate configurations. Further the through-bores may be axially aligned or axially offset and may be dispose at various aligned or non-aligned angles.

Figure 18A:
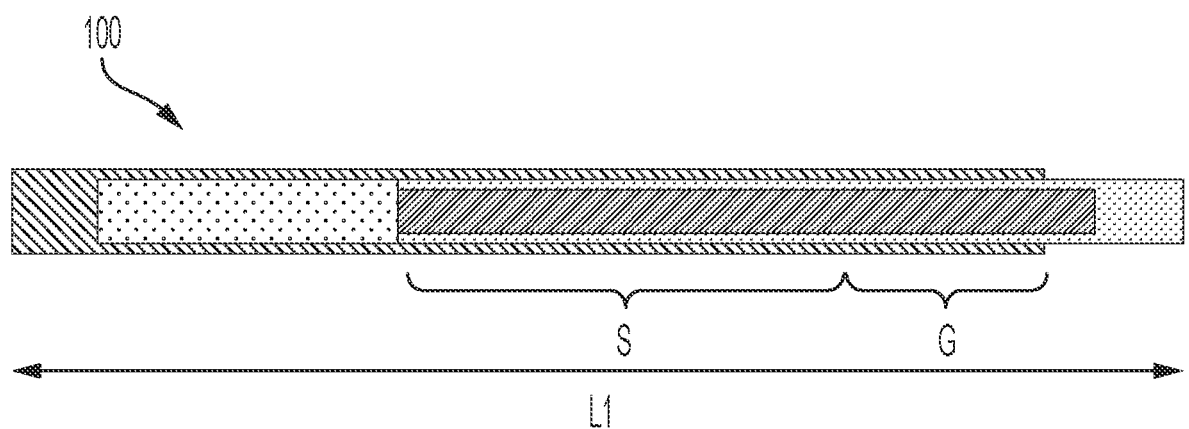
FIGS. 18A and 18B are comparative views of a prior art device (18A) and the device in accordance with the present invention (18B) illustrating the compact length of the present invention in the retracted configuration.
Figure 18B:
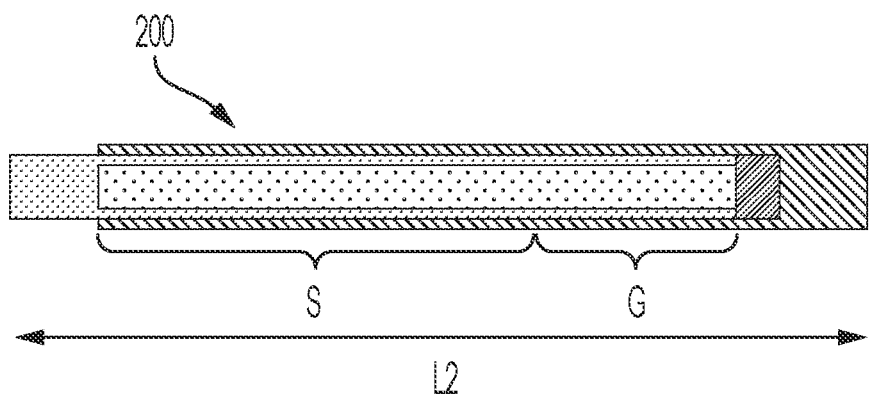

Referring now to FIGS. 18A and 18B, one advantage of bone lengthening devices 200 in accordance with the present are illustrated. In the comparative views shown in FIGS. 18A and 18B, the bone lengthening device 200 of the present invention has a minimum (e.g., fully retracted) length L2 that is significantly shorter than the minimum (e.g., fully retracted) length L1 of a bone lengthening device 100 consistent with the prior art, while having the same stroke length S and guiding length G. The shorter overall retracted length is important as it allows the bone lengthening device 200 of the present invention to be used on smaller bones present when treating pediatric patients.

Figure 19A:
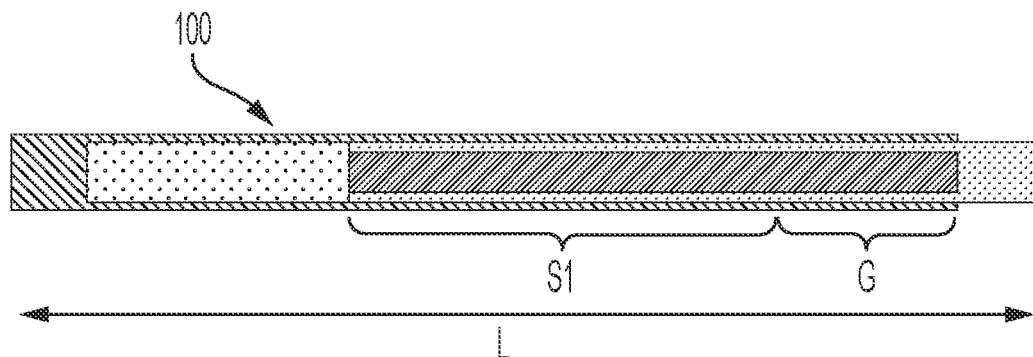
FIGS. 19A and 19B are comparative views of a prior art device (19A) and the device in accordance with the present invention (19B) illustrating the longer stroke length achieved by the present invention.
Figure 19B:
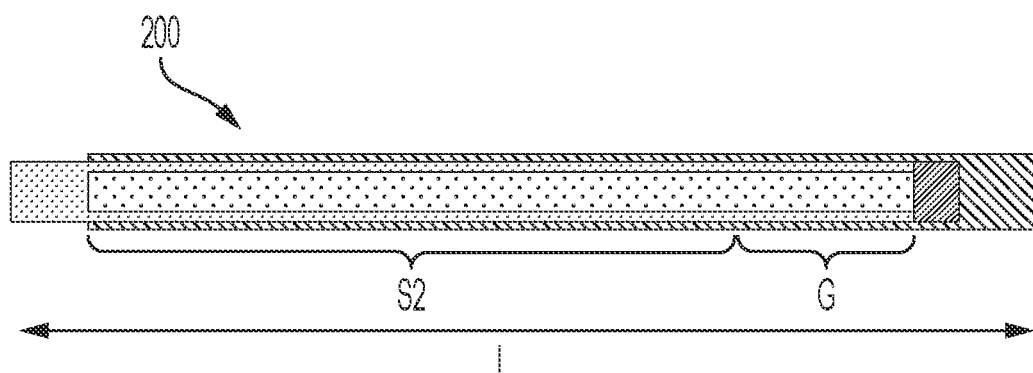

FIGS. 19A and 19B, illustrate another advantage of bone lengthening device 200. In these comparative views, the stroke length S2 of a bone lengthening device 200 in accordance with the present invention is significantly longer than the stroke length S1 of a bone lengthening device 100 of the prior art that has the same minimum (e.g., retracted) length L and the same guiding length G.

Figure 20A:
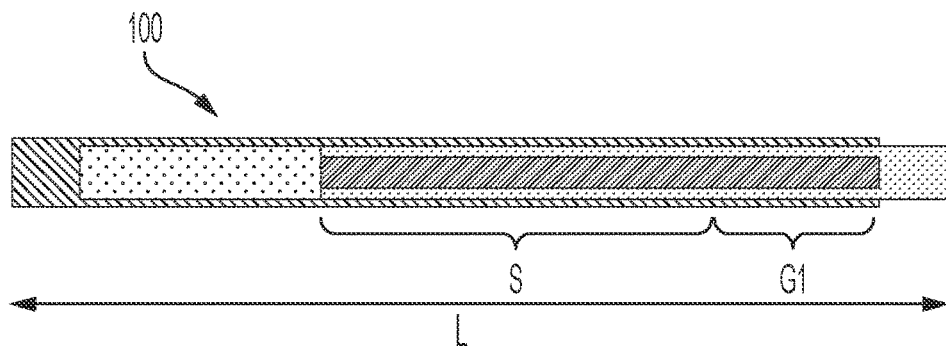
FIGS. 20A and 20B are comparative views of a prior art device (20A) and the device in accordance with the present invention (20B) illustrating the longer guiding length achieved by the present invention for the same stroke length achieved by a prior art device.
Figure 20B:
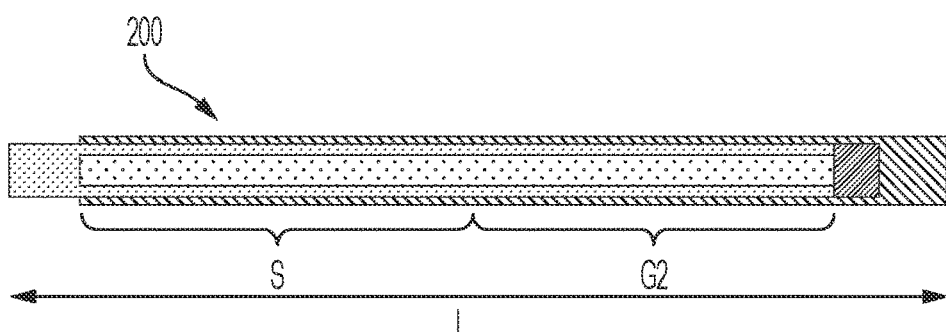

FIGS. 20A-20B illustrate another advantage of bone lengthening devices 200 in accordance with the present invention. In these comparative views, guiding length G2 of a bone lengthening device 200 consistent with the present disclosure is significantly longer than the guiding length G1 of a bone lengthening device 100 of the prior art that has the same minimum (e.g., retracted) length L and the same stroke length S.

Figure 21A:
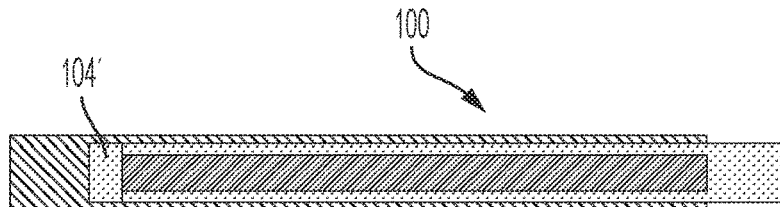
FIGS. 21A and 21B are comparative views of a prior art device (21A) and the device in accordance with the present invention (21B) illustrating the greater internal volume available for housing electro-mechanical systems in the present invention as compared with the prior art device.
Figure 21B:
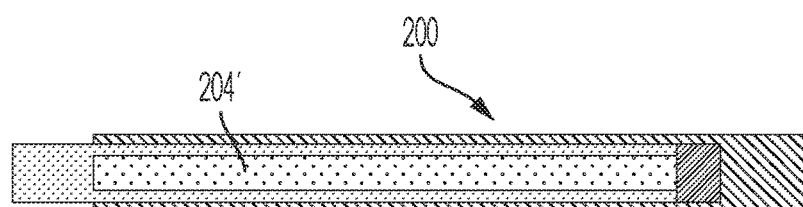

FIGS. 21A and 21B, illustrate yet another advantage of bone lengthening device 200 of the present disclosure. In this comparative view, the space 204' available for a rotational actuator in a bone lengthening device 200 of the present disclosure (FIG. 21B) is substantially greater than the space 104' available for an actuator in systems of the prior art (FIG. 21A).

Figure 22:
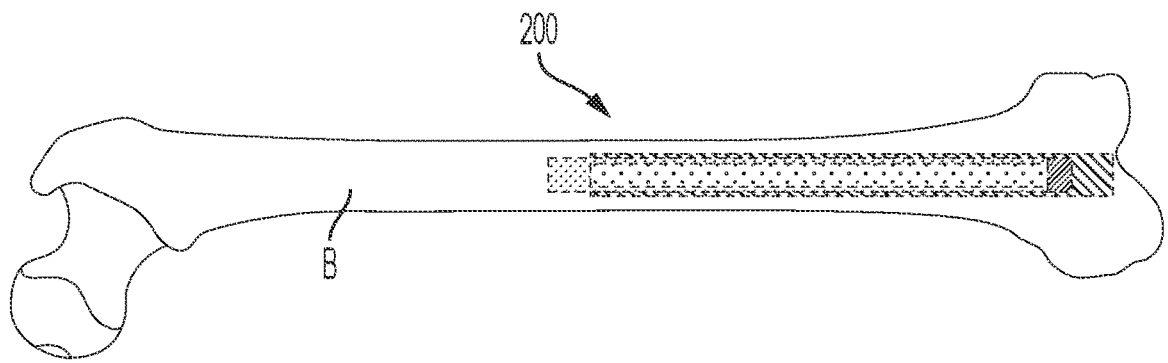
FIG. 22 illustrates use of a bone lengthening device in accordance with the present invention as an intramedullary lengthening device.
Figure 23:
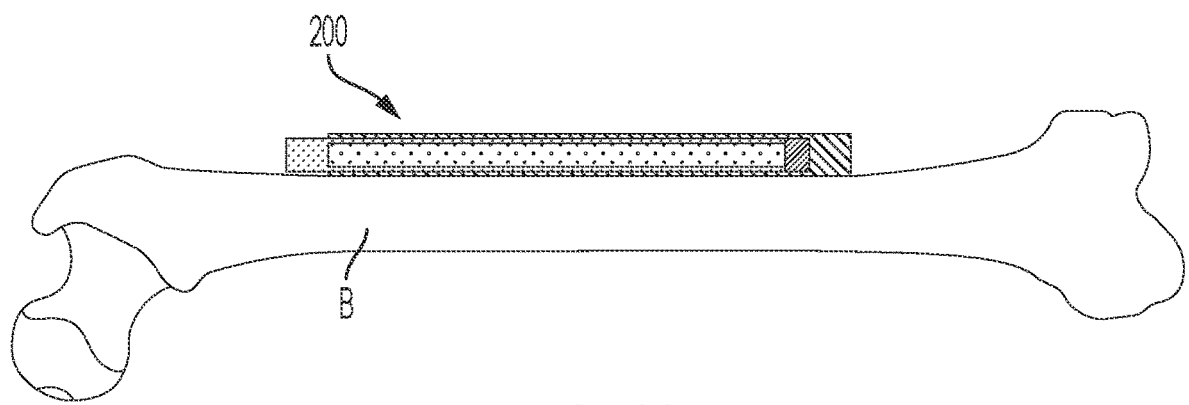
FIG. 23 illustrates use of a bone lengthening device in accordance with the present invention as an extramedullary lengthening device.
Figure 24:
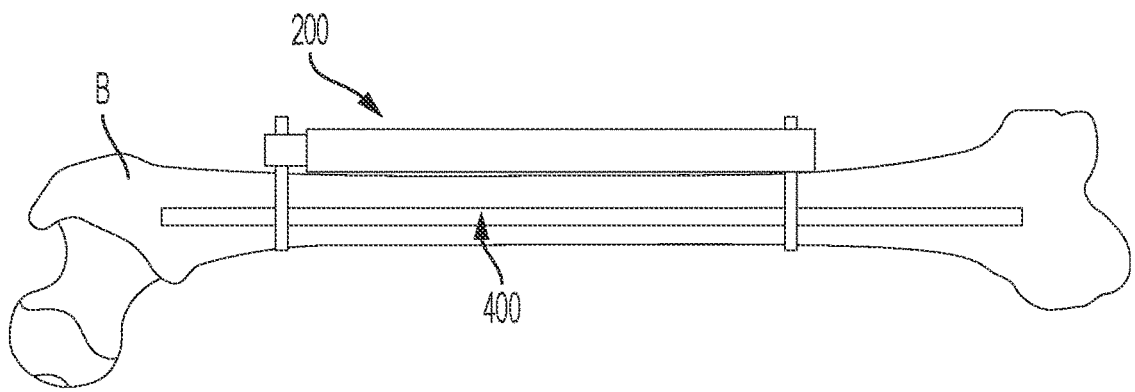
FIG. 24 illustrates use of a bone lengthening device in accordance with the present invention as an extramedullary lengthening device associated with an intramedullary stiffener.
Figure 25:
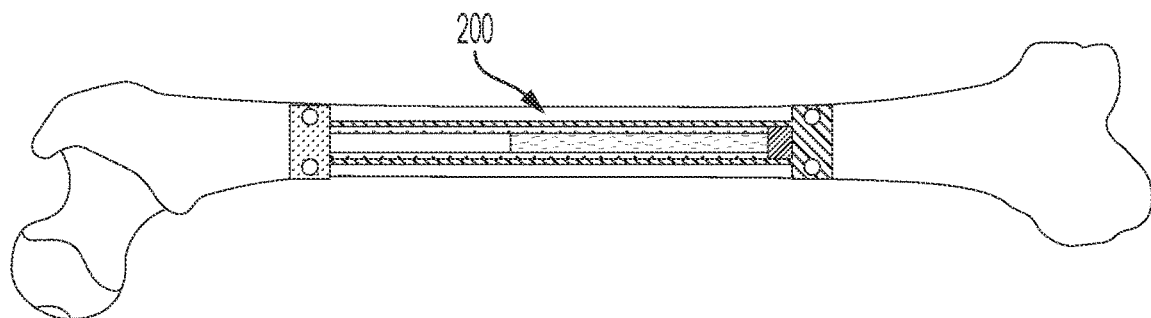
FIG. 25 illustrates another example of a bone lengthening device in accordance with the present invention as an extramedullary lengthening device.

FIG. 22 illustrates a bone lengthening device 200 of the present disclosure used as intramedullary lengthening device. Referring to FIG. 23, the bone lengthening devices 200 of the present disclosure can be use as extramedullary lengthening devices. Referring to FIG. 24, the bone lengthening devices 200 of the present disclosure when used as extramedullary lengthening devices can be associated with an intramedullary stiffener 400. Referring to FIG. 25, the bone lengthening devices 200 of the present disclosure can be used as a lengthening plate. In some embodiments, the implantable bone lengthening device 200 is an intramedullary retrograde nail, while in other embodiments the implantable bone lengthening device is an intramedullary antegrade nail.

Figure 26:
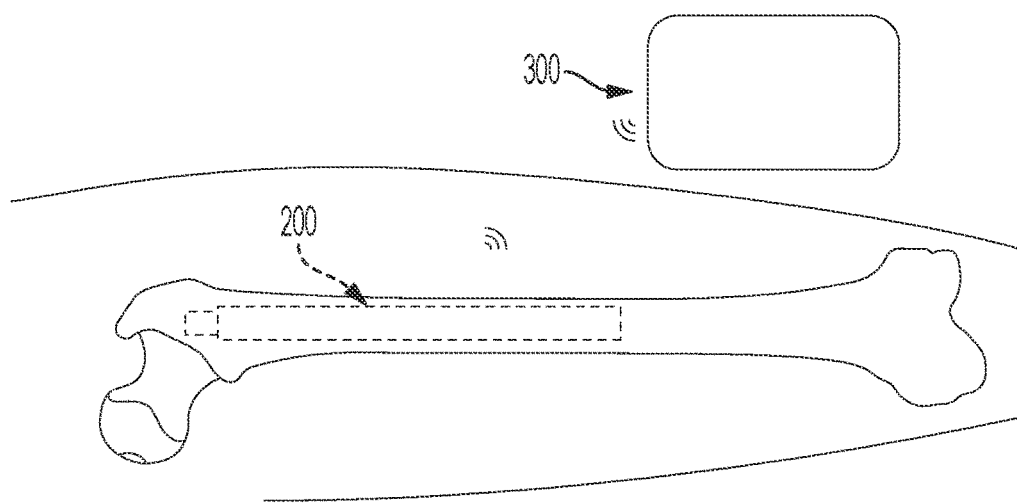
FIG. 26 illustrates an embodiment of a bone lengthening device in accordance with the present invention in wireless communication with an external control unit.
Figure 27:
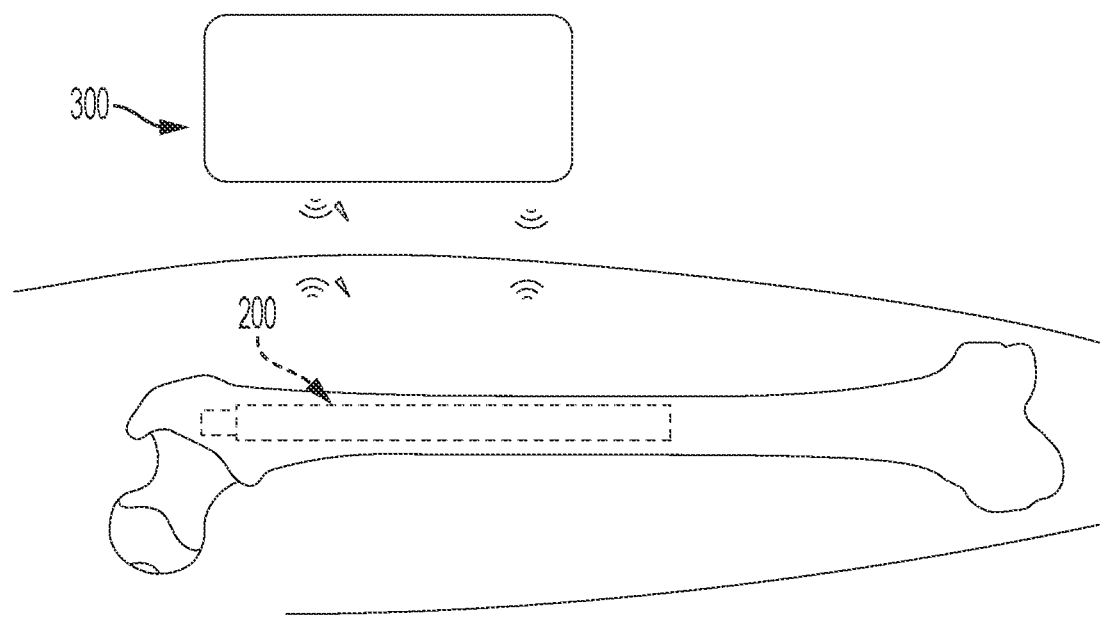
FIG. 27 illustrates an embodiment of a bone lengthening device in accordance with the present invention configured for receiving power wirelessly and in wireless communication with an external control unit.
Figure 28:
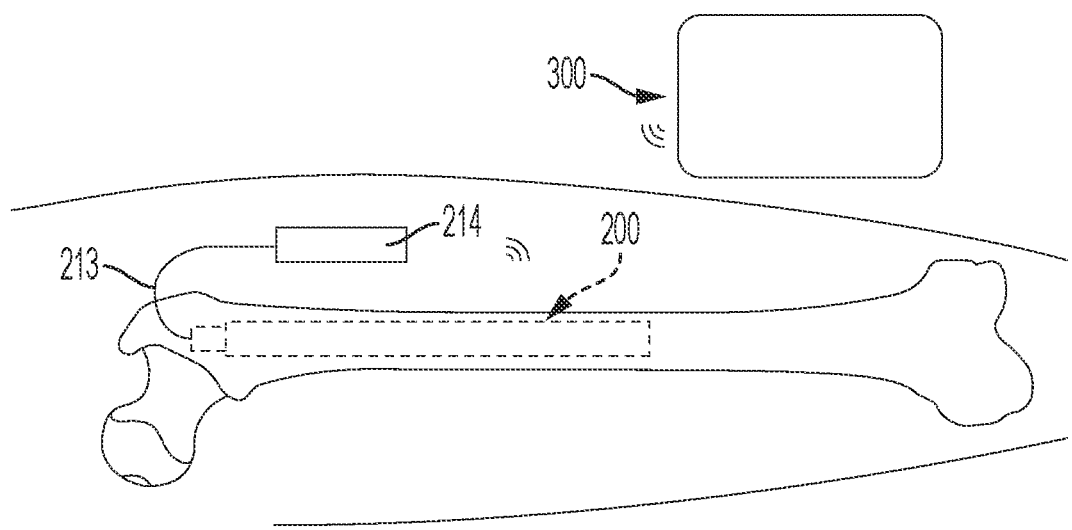
FIG. 28 illustrates an embodiment of a bone lengthening device in accordance with the present invention wired to an implantable powering module and configured for wireless external control.
Figure 29:
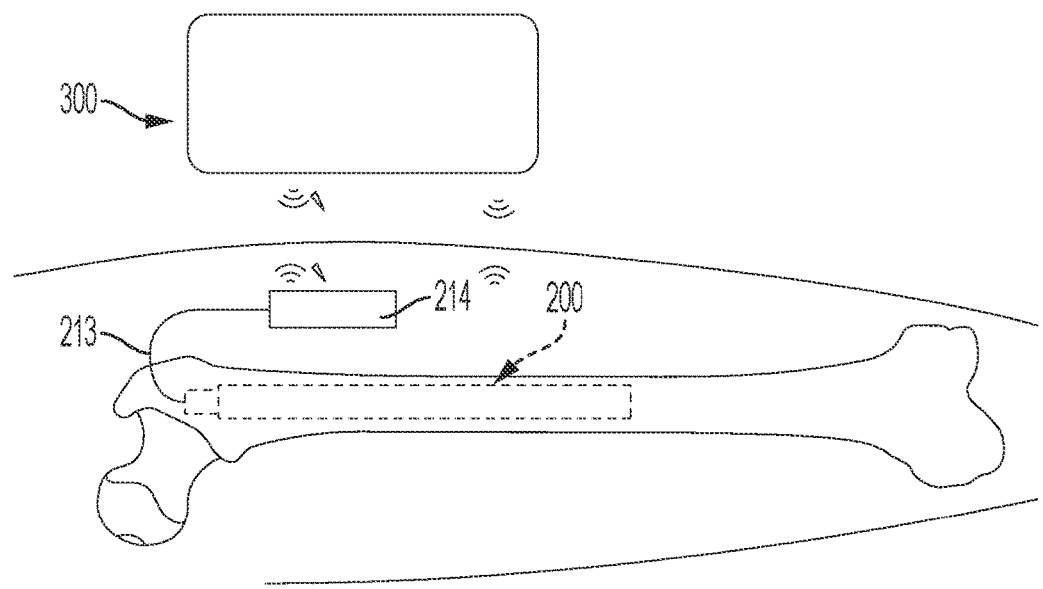
FIG. 29 illustrates an embodiment of a bone lengthening device in accordance with the present invention wired to an implantable power receiving module and configured for wireless external control.

In the case represented by FIG. 26, the implantable bone lengthening device 200 is powered by an integrated power source as disclosed above and wirelessly communicates with the external control unit 300. Wireless communications may include transmission of signals to external and/or from control unit 300, or some other electronic monitoring and/or control device. In addition, wireless communications may include receipt by device 200 of transmitted signals from external control unit 300, or some other electronic monitoring and/or control device. FIG. 27 illustrates the implantable bone lengthening device 200 receiving power using an integrated power receiver as disclosed above whereby device 200 is wirelessly powered by, and communicates wirelessly with, the external control unit 300. In accordance with this embodiment, electrical power is wirelessly transmitted to device 200 via external control unit 300. FIG. 28 illustrates an embodiment wherein implantable bone lengthening device 200 is powered by a remote powering module 214 (equipped with a power storage and/or a battery power source) and wirelessly communicates with an external control unit 300. In the case represented by the FIG. 29, the implantable bone lengthening device 200 is powered by the remote powering module 214 which is equipped with a power receiver to receive energy wirelessly from external control unit 300, whereby electrical energy may be supplied to device 200 via electrically conducting cable 213. This embodiment further includes (a) the capability of wired communication between device 200 and module 214; (b) wireless communication between module 214 and external control unit 300. The present invention further contemplates that cable 213 my further include at least a portion thereof configured as a wireless communications antenna. As should be apparent, the control unit 300 provides a signal to the implantable bone lengthening device 200 (e.g., to the rotational actuator 204) to rotate the lead screw 206. In some embodiments, the signal includes sufficient information to cause the rotational actuator 204 to rotate the lead screw 206 by a predetermined amount (e.g., by a predetermined rotational degree of the lead screw 206, a predetermined axial movement of the outer rod 208, a predetermined torque or a predetermined force). In some embodiments, the signal includes a power component, such as a voltage wave or some alternating current waves.

Figure 30A:
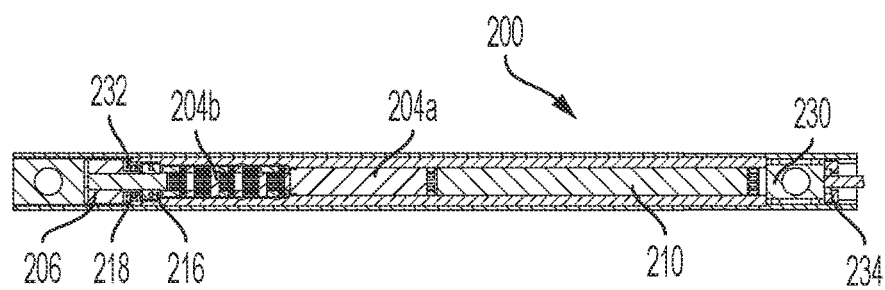
FIGS. 30A and 30B are cross-section illustrations of a bone lengthening device in accordance with the present invention in both the retracted and extended configurations.
Figure 30B:
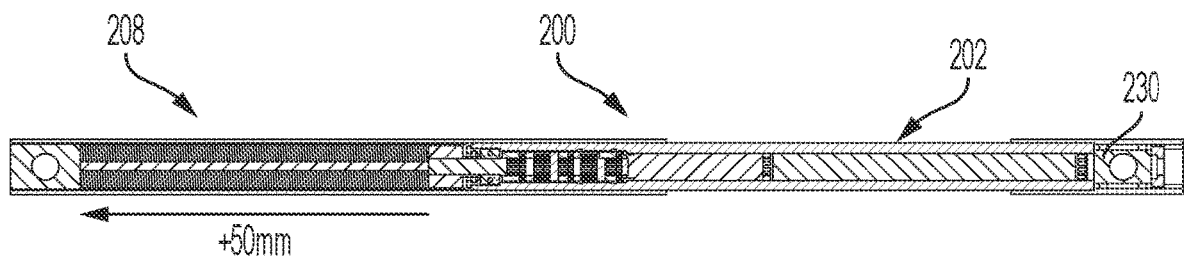
Figure 31A:
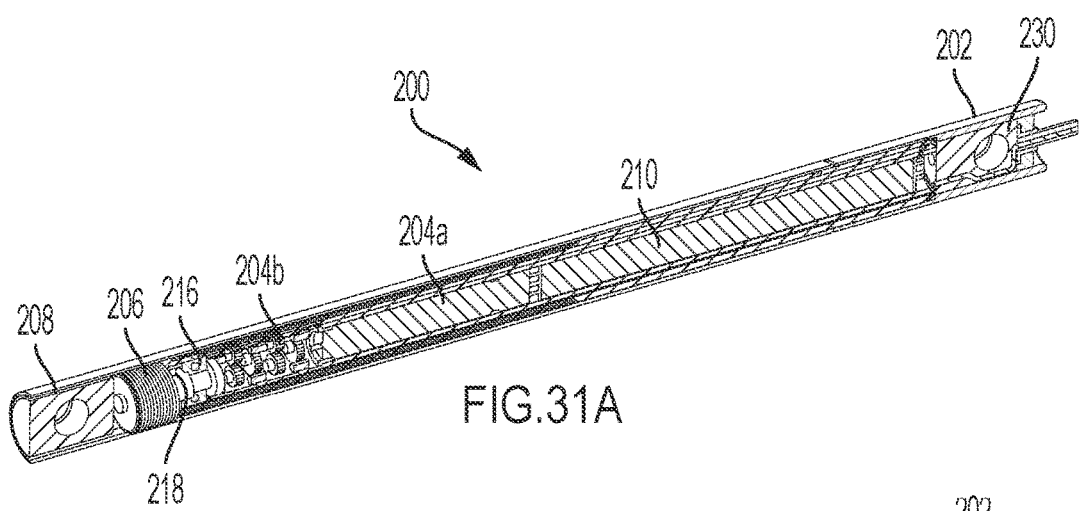
FIGS. 31A and 31B are perspective cross-sectional illustrations of a bone lengthening device in accordance with the present invention in both the retracted and extended configurations.
Figure 31B:
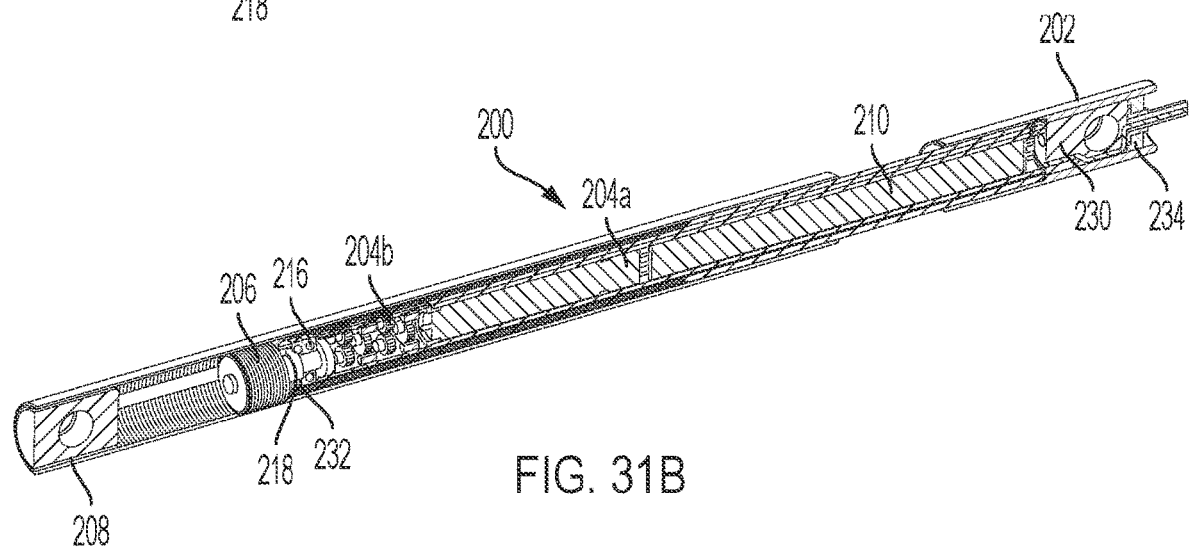
Figure 32:
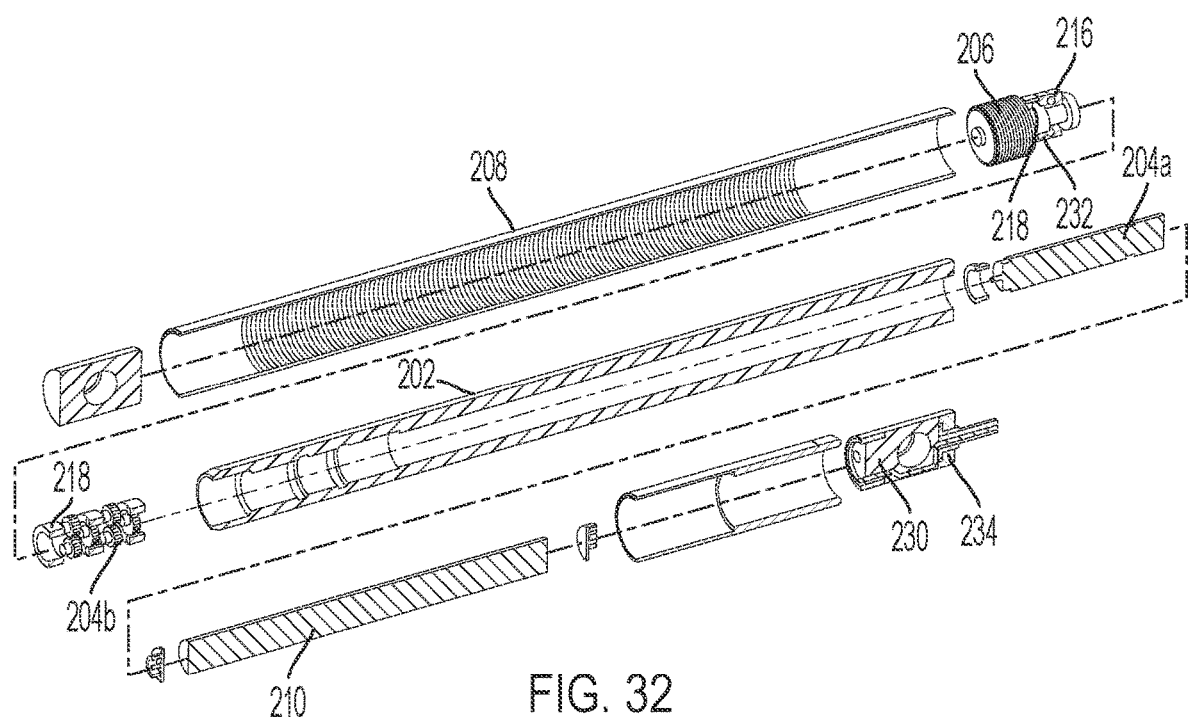
FIG. 32 is an exploded perspective cross-sectional illustration of a bone lengthening device in accordance with the present invention.

FIGS. 30A and 30B are sectional views of a bone lengthening device 200 in accordance with the present invention illustrating the device in retracted and extended configurations respectively and further illustrating 50.0 mm of travel between the retracted and extended configurations. FIGS. 31A and 31B are sectional perspective views depicting bone lengthening device 200 in retracted and extended configurations. Bone lengthening device 200 includes an inner rod 202 and an outer rod 208 disposed in telescopically expandable relation. Housed within inner rod 202 there is an actuating assembly 204 which includes a motor 204*a* driving a gear box 204*b* which in turn drives lead screw 206. A bearing 216 and seal 218 are disposed between gearbox 204*b* and lead screw 206. Inner rod 202 further houses an electronics package 210 which is in electronic communication with motor 204*a* via electrical connection on one side thereof, and a sensor 230 via electrical connection on an opposing side thereof. Sensor 230 functions to detect and measure axial forces applied to the bone lengthening device 200. Device 200 further includes a proximal axial stop 232 and an antegrade axial stop 234. Proximal axial stop 232 functions to close off the proximal extremity of the device and retain axial pulling forces. For example, when a surgeon applies a tensile force to the end 202a of inner rod 202 the force is transmitted to the outer rod 208 via lead screw 206, bearing 216, and axial stop 232. The antegrade axial stop 234 is associated with sensor 230. FIG. 32 is an exploded perspective cross-sectional illustration of a bone lengthening device in accordance with the present invention.

In a contemplated alternate embodiment, implantable bone elongating device may further include a vibration sensor configured to detect vibration patterns linked to callus stiffness and/or to implantable bone elongation device performance.

Figure 33:
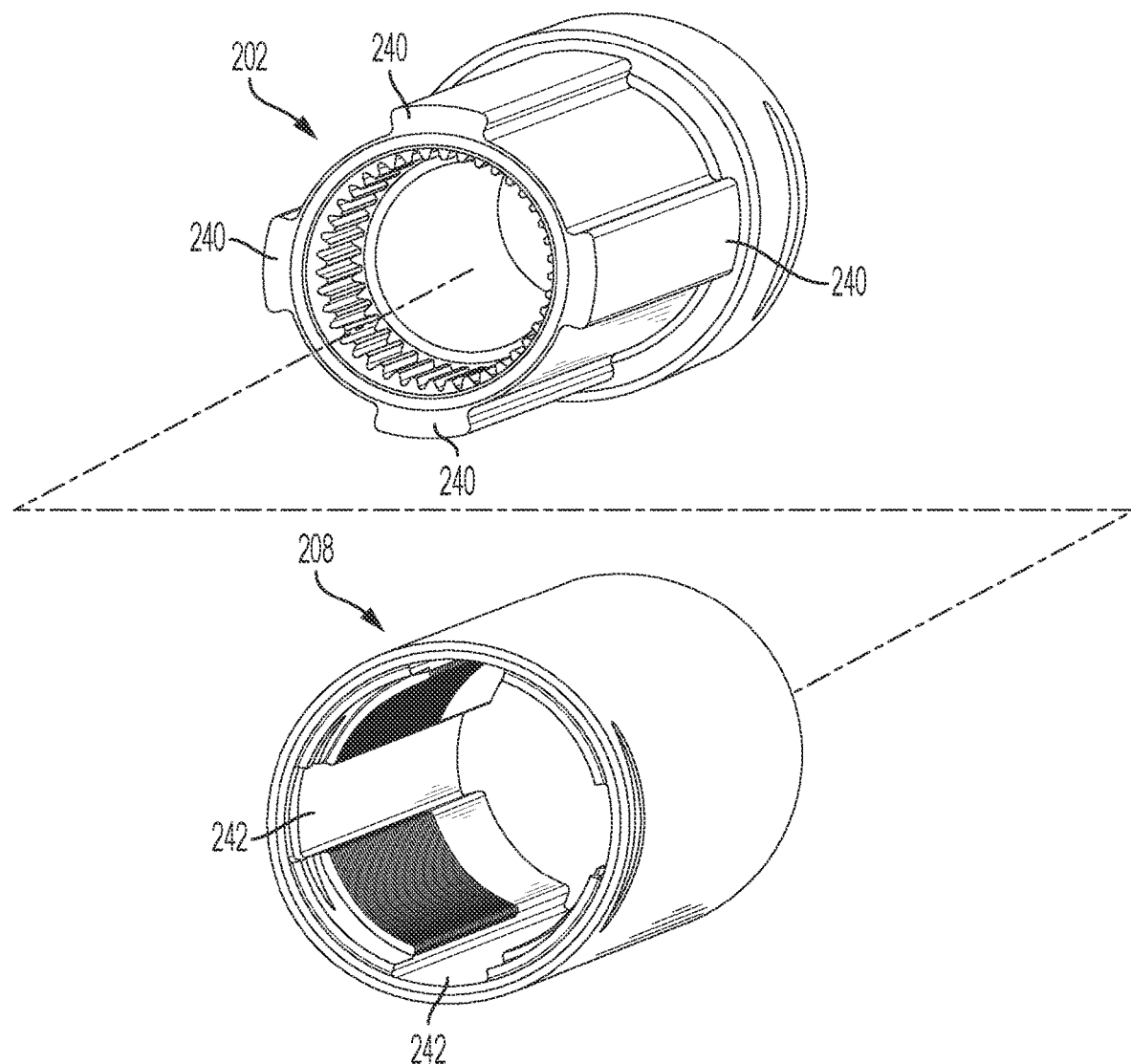
FIG. 33 is a partial perspective exploded view of inner and outer rod lugs for restricting rotational movement between the inner and outer rods.
Figure 34:
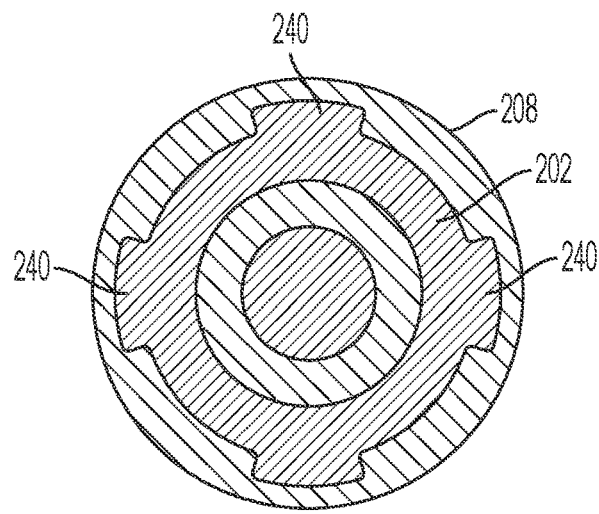
FIG. 34 is a sectional view illustrating mating engagement of the inner and outer rod lugs.
Figure 35:
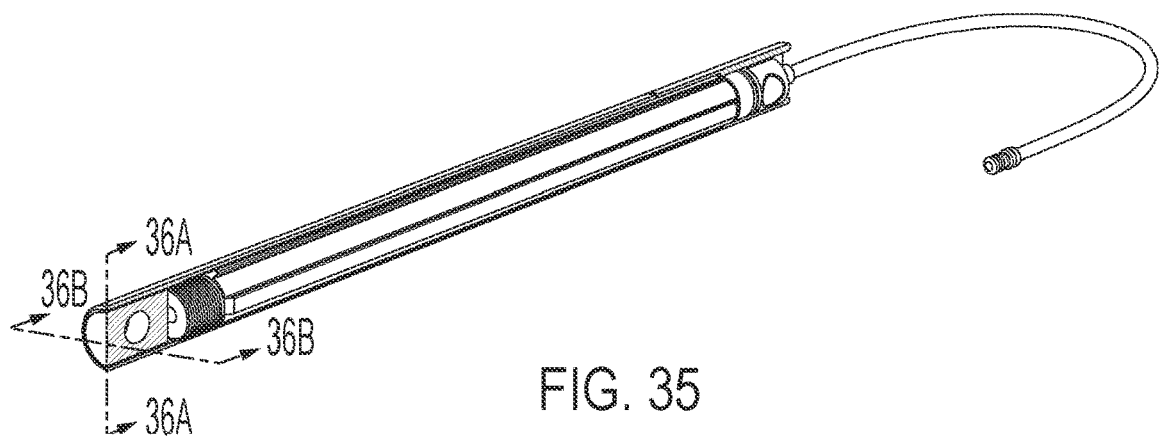
FIG. 35 is a partial cross-sectional view of the device illustrating the inner rod lugs.
Figure 36A:
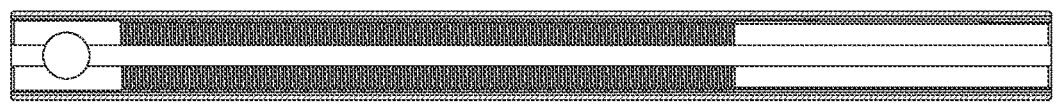
FIG. 36A is a cross-sectional view taken along line 36A-36A in FIG. 35 illustrating the partially threaded inner surface of the outer rod.
Figure 36B:
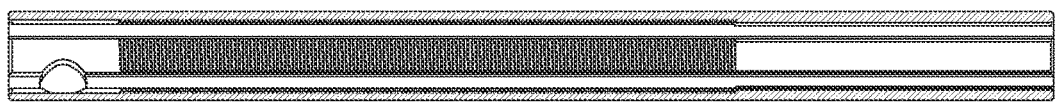
FIG. 36B is a cross-sectional view taken along line 36B-36B in FIG. 35 illustrating the partially threaded inner surface of the outer rod.
Figure 37A:
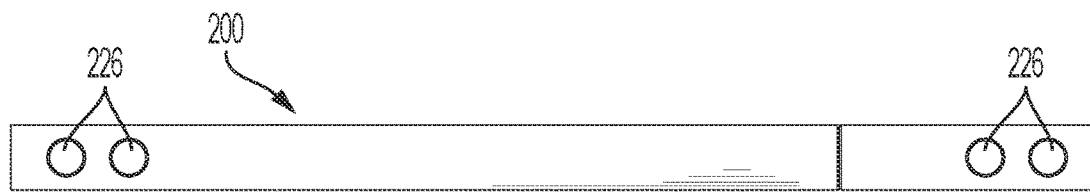
FIG. 37A is a side view illustrating through bores disposed at opposing ends of the device.
Figure 37B:
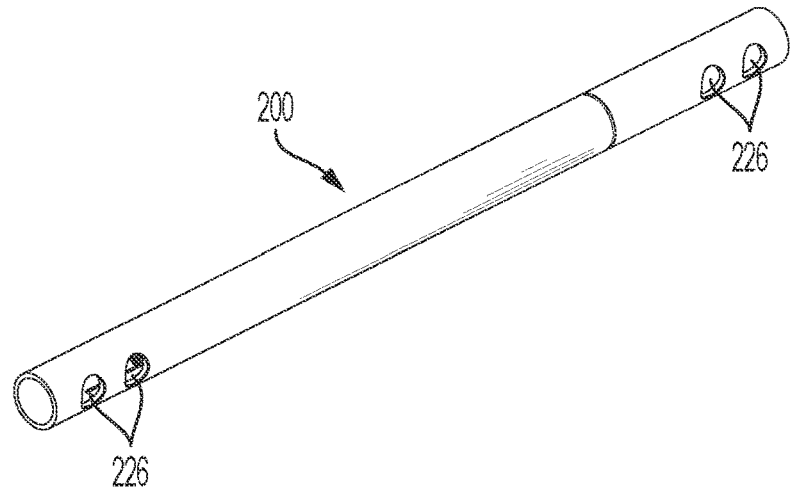
FIG. 37B is a perspective view thereof.
Figure 38A:
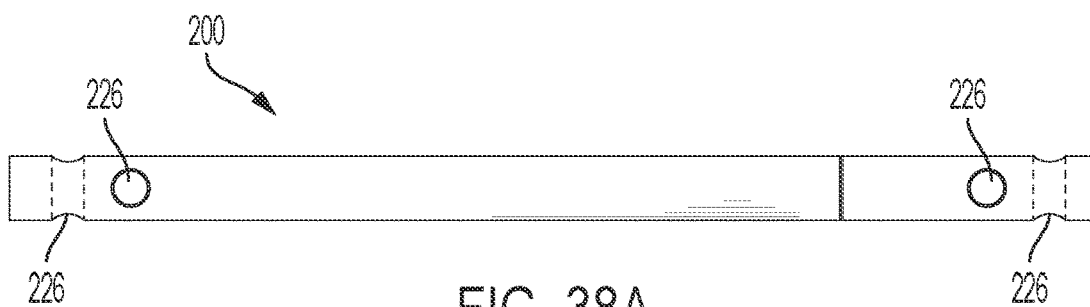
FIG. 38A is a side view illustrating an alternate through bore configuration at opposing ends of the device.
Figure 38B:
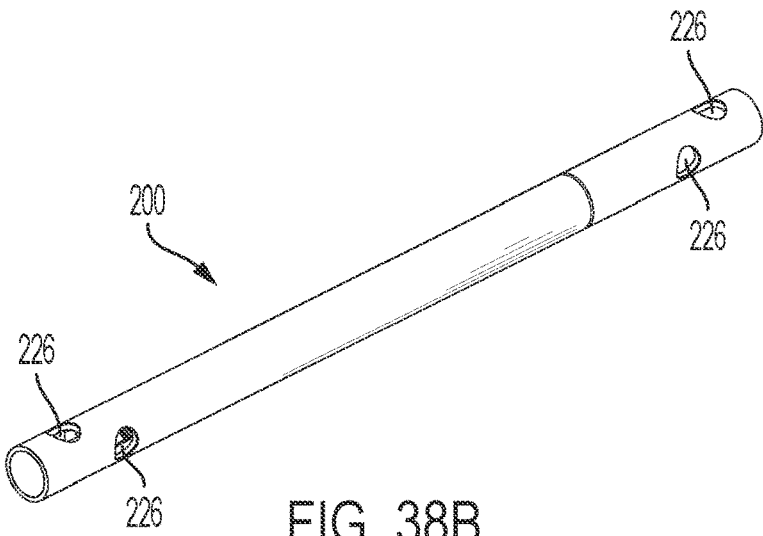
FIG. 38B is a perspective view thereof.
Figure 39:
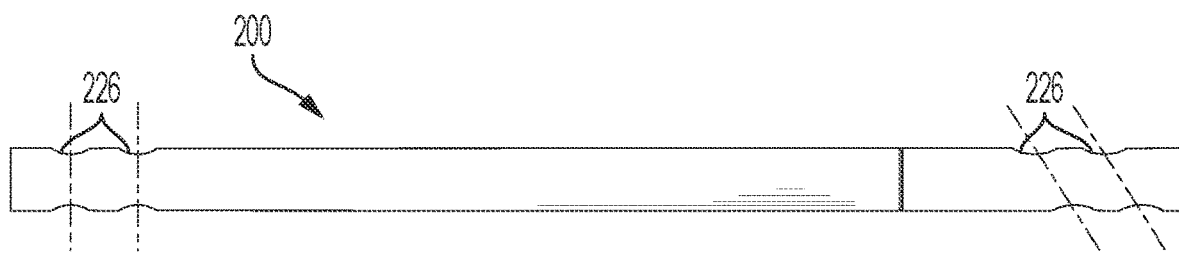
FIG. 39 is a side view illustrating through bores configured at perpendicular and oblique angles.

Turning now to FIG. 33, there is depicted structure for restricting rotational movement between the inner and outer rods, namely the outer surface of the inner rod 202 defines one or more radially outwardly projecting and longitudinally disposed lugs, referenced as 240, and the inner surface of outer rod 208 defines one or more radially inwardly projecting and longitudinally disposed channels, referenced as 242. Lugs 240 are received within channels 242 when the inner rod 202 is operatively engaged with outer rod 208. FIG. 34 is a cross-sectional illustration showing inner rod 202 disposed within outer rod 208 with lugs 240 slidably received within channels 242. As should be apparent with lugs 240 received within channels 242, the inner 202 and outer rod 208 are capable of longitudinal telescopic expansion and contraction while being prevented from rotation relative to each other. FIG. 35 provides an additional longitudinal sectional view of the device illustrating the inner rod lugs 240. Lugs 240 and channels 242 may extend substantially the entire length of the device 200 or may extend only partially, and further may be continuous formed in spaced segments. FIG. 36A is a cross-sectional view taken along line 36A-36A in FIG. 35 illustrating a channel 242 formed in the partially threaded inner surface of the outer rod 208. FIG. 36B is a cross-sectional view taken along line 36B-36B in FIG. 35 illustrating the partially threaded inner surface of the outer rod 208. FIG. 37A illustrates through bores 226 disposed at opposing ends the device 200 wherein the through bores are longitudinally spaced and in axial parallel alignment, and FIG. 37B is a perspective view thereof. FIG. 38A is a side view illustrating an alternate through bore configuration wherein through bores at opposing ends of device 200 longitudinally spaced with axis angularly offset, and FIG. 38B is a perspective view thereof. FIG. 39 is a side view illustrating through bores configured at perpendicular and oblique angles.

Figure 40A:
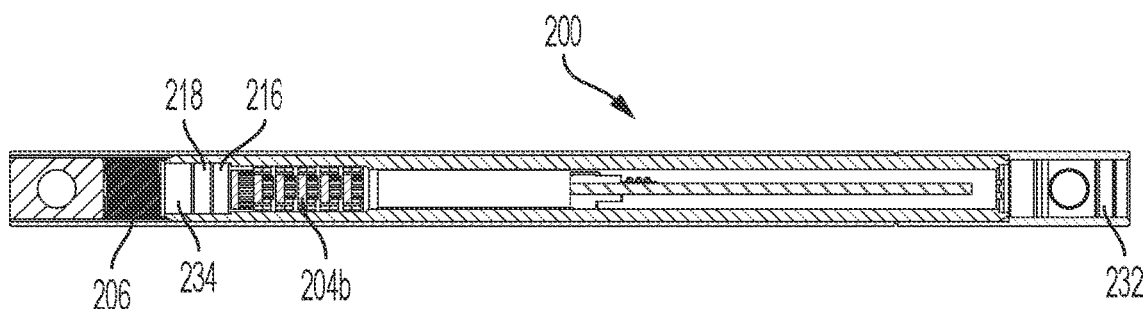
FIG. 40A is a side sectional view highlighting the distal and proximal axial stops.
Figure 40B:
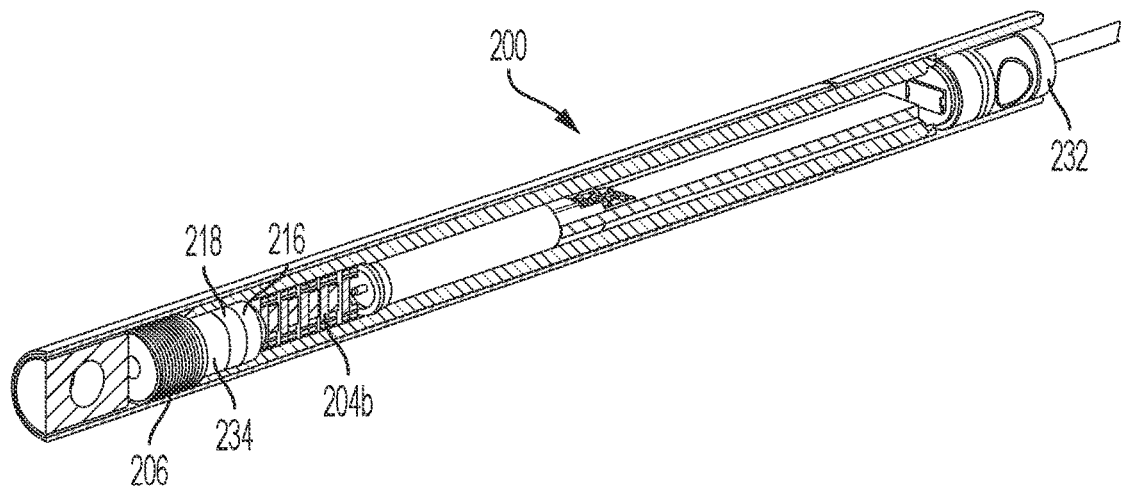
FIG. 40B is a perspective sectional view thereof.
Figure 41:
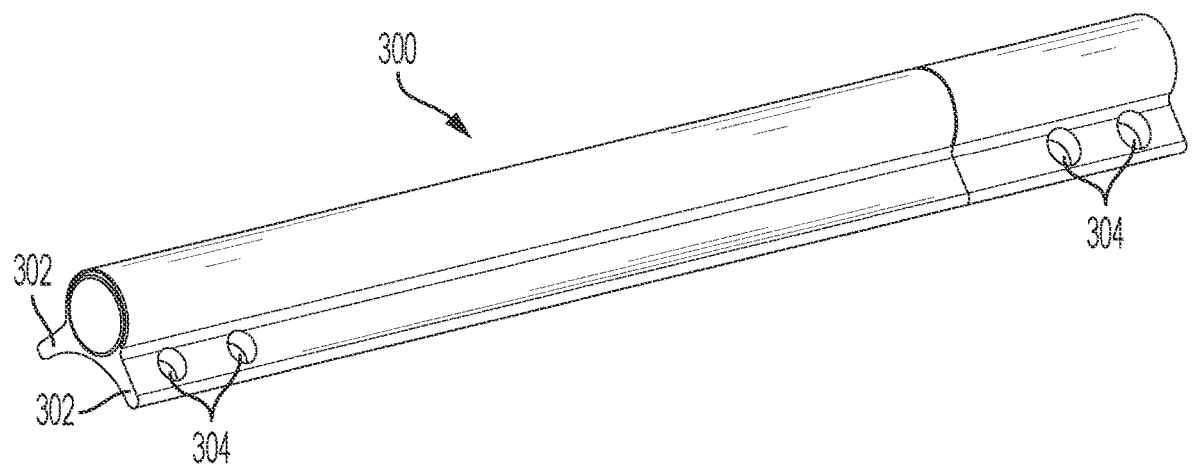
FIG. 41 illustrates an alternate configuration of the device with through bores defined in projecting flanges.

FIG. 40A is a side sectional view highlighting the proximal axial stop 232 and the distal axial stop 234 proximal axial stop, and FIG. 40B is a perspective sectional view thereof. FIG. 41 illustrates an alternate embodiment configuration of a bone elongating device, generally referenced as 300. Alternate embodiment bone elongating device 300 has substantially identical components and functions as bone elongating device 200, but further includes longitudinally disposed projecting flanges, referenced as 302. Each flange 302 defines one or more through bores 304 which function to receive fasteners or sutures (not shown) to affix device 300 to bone.

Methods of Lengthening Bones

Implantable bone lengthening devices 200 consistent with the present disclosure may be used to lengthen a bone of a subject in need thereof, such as a pediatric subject. In general, methods of lengthening a bone in a subject in need thereof comprise: associating (e.g., implanting) an implantable bone lengthening device 200 as disclosed herein with a bone of the subject that requires lengthening, activating the rotational actuator 204a of the implantable bone lengthening device 200 to lengthen the implantable bone lengthening device 200, waiting a period of time for bone formation (e.g., callus bone) to occur, and repeating the activation and waiting steps until the bone has been lengthened a desired amount. In some embodiments, the method further comprises removing the implantable bone lengthening device 200 from the subject after the bone has been lengthened the desired amount.

In some embodiments, the step of associating the implantable bone lengthening device 200 comprises inserting the bone lengthening device 200 into a medullary cavity of a bone. In some embodiments, the medullary cavity is expanded (e.g., drilled) to accommodate the diameter and/or the length of the implantable bone lengthening device 200. The step of associating (e.g., implanting) the implantable bone lengthening device 200 may further comprise anchoring the inner rod 202 to the bone, for example by one or more bone screws, bone anchors, and/or sutures; and anchoring the outer rod 208 to the bone, for example by one or more bone screws, bone anchors, and/or sutures. In some embodiments, the step of anchoring the inner rod 202 to the bone comprises driving one or several bone screws through one or several holes 226. In some embodiments, the step of anchoring the inner rod 202 to the bone comprises driving two or more bone screws through the holes 226 through lateral fixation plate 228 associated with the inner rod 202. In some embodiments, the step of anchoring the outer rod 208 to the bone comprises driving one or several bone screws through one or several holes 226 of the outer rod 202. In other embodiments, the step of anchoring the outer rod 208 to the bone comprises driving two or more bone screws through the holes 226 through lateral fixation plate 228 associated with the outer rod 202.

As shown in FIG. 22, the step of associating the implantable bone lengthening device 200 with the bone B may comprise inserting the implantable bone lengthening device 200 into the medullary cavity of the bone B. In other embodiments, such as those consistent with FIG. 23, the step of associating the implantable bone lengthening device 200 with the bone B comprises attaching the implantable bone lengthening device 200 with the external surface (e.g., cortical surface) of the bone B. In such embodiments bone screws or threading sutures (not shown) are driven or passed through through-bores 226 of the inner rod 202, and by driving bone screws or threading sutures through the holes 226 of outer rod 208, using for example the embodiment depicted in previously discussed FIG. 17.

As illustrated in the embodiment depicted in FIG. 24, in an extramedullary configuration of the device 200, a stiffener 400 may be intramedullary associated with the bone B to provide stabilization and rigidity. Stiffener 400 is sized, shaped, and associated with the bone B to further stabilize the bone B by reducing or eliminating the risk of the bone B bending along its length. In some embodiments, the method further comprises performing a corticotomy and/or an osteotomy on the bone before associating the implantable bone lengthening device 200 with the bone.

The step of activating the rotational actuator 204 comprises sending an electrical signal to the rotational actuator 204, for example from the control unit 300, to cause the lead screw 206 to extend the outer rod 208 by a predetermined distance relative to the inner rod 202. The predetermined distance could be from 0.01 mm to 2.0 mm, however, any suitable distance is considered within the scope of the present invention. In some embodiments, the step of activating the rotational actuator 204 comprises sending an electrical signal to the rotational actuator 204, for example from the control unit 300, to cause the lead screw 206 to extend the outer rod 208 by a predetermined force relative to the inner rod 202. The predetermined force could be from 1N to 3000N. In some embodiments, the step of activating the rotational actuator 204 comprises sending an electrical signal to the rotational actuator 204, for example from the control unit 300, to cause the lead screw 206 to extend the outer rod 208 by a predetermined force derivative relative to the inner rod 202. The predetermined force variation (i.e. derivative could be from 4 N/mm to 50000 N/m. This step of activating the rotational actuator to either extend outer rod 208 by a predetermined distance or to apply a predetermined force is preferably repeated in a sequential predetermined manner.

In some embodiments, the step of activating the rotational actuator 204 comprises sending an electrical distraction signal to the rotational actuator 204 from the control unit 300. The distraction signal causes the lead screw 206 to extend the outer rod 208 by a combination of predetermined distance, force and force variation. In some embodiments predetermined distance, force and force variation can be achieved with a predetermined speed or a predetermined time, or a maximum/minimum speed or time. In some embodiments, the step of waiting a period of time to enable formation of callus bone comprises waiting from few seconds to several hours or even days. In some embodiments, the step of activating the rotational actuator and the step of waiting a period of time to enable callus bone to form operate together to distract the bone about 0.25 mm per day to about 2 mm per day. The steps of activating the rotational actuator and waiting for a period of time are repeated until the bone has been lengthened by a desired amount. The desired amount of lengthening will vary from subject to subject, and from bone to bone.

In some embodiments, the present disclosure provides a method of lengthening a bone B of a subject in need thereof, the method comprising: (a) associating an implantable bone lengthening device 200 as disclosed herein with a bone B of the subject; (b) activating the rotational actuator 204 to advance the outer rod 208 relative to the inner rod 202 by a predetermined distance, force, force derivative, speed and/or time; (c) waiting a period of time to enable formation of callus bone; and (d) repeating steps (b)-(c) until the bone B has lengthened by a desired length. In some embodiments, the method further comprises forming or expanding a medullary cavity in the bone before the step of associating the implantable bone lengthening device 200 with the bone B. In some embodiments, the method further comprises associating a stiffener 400 with the bone B to further stabilize the bone B. In some embodiments, the step of associating the implantable bone lengthening device 200 with the bone B comprises inserting the implantable bone lengthening device 200 into a medullary cavity in the bone B. In some embodiments, the step of associating the implantable bone lengthening device 200 with the bone B comprises attaching the implantable bone lengthening device 200 to an exterior surface of the bone B. In some embodiments, the subject is a pediatric subject. In some embodiments, in some embodiments, the bone B is a lower limb bone the bone B is an upper limb bone.

The invention includes embodiments where the invention is an apparatus for correction of a Scoliotic curve in a spine comprising an inner rod and a tubular outer rod isolated completely under the skin; attachment screws to couple the said inner rod and said tubular outer rod to the spine wherein an end of said inner rod is coupled to a first vertebra, and an opposing end of said outer rod is coupled to a second vertebra; further comprising rotational actuator housed within said inner rod, to longitudinal extend the device over an extended defined period of time under external control until a desire spinal curve is obtained as otherwise generally set forth herein above. The apparatus is combined with an external or implantable source of power, and in one embodiment the device further comprises a link with sensor means allowing the measurement of the driving force, and/or the elongation vector as disclosed herein. In one embodiment of the invention, the said sensor means is composed of at least one strain gauge for Force measurements. In one embodiment of the invention, the sensor means is composed of at least one accelerometer for displacement measurements. More generally, where the invention is characterized as a combination of a tubular outer rod, an inner rod, attachment screws, a rotational actuator housed in the said inner rod, where a lead screw rotationally coupled to said rotational actuator, said lead screw in threaded engagement with the threaded inner surface of said outer rod produces a force over a defined period of time until the spine to which the force is steadily applied straightens at least to a partial degree.

Figure 42:
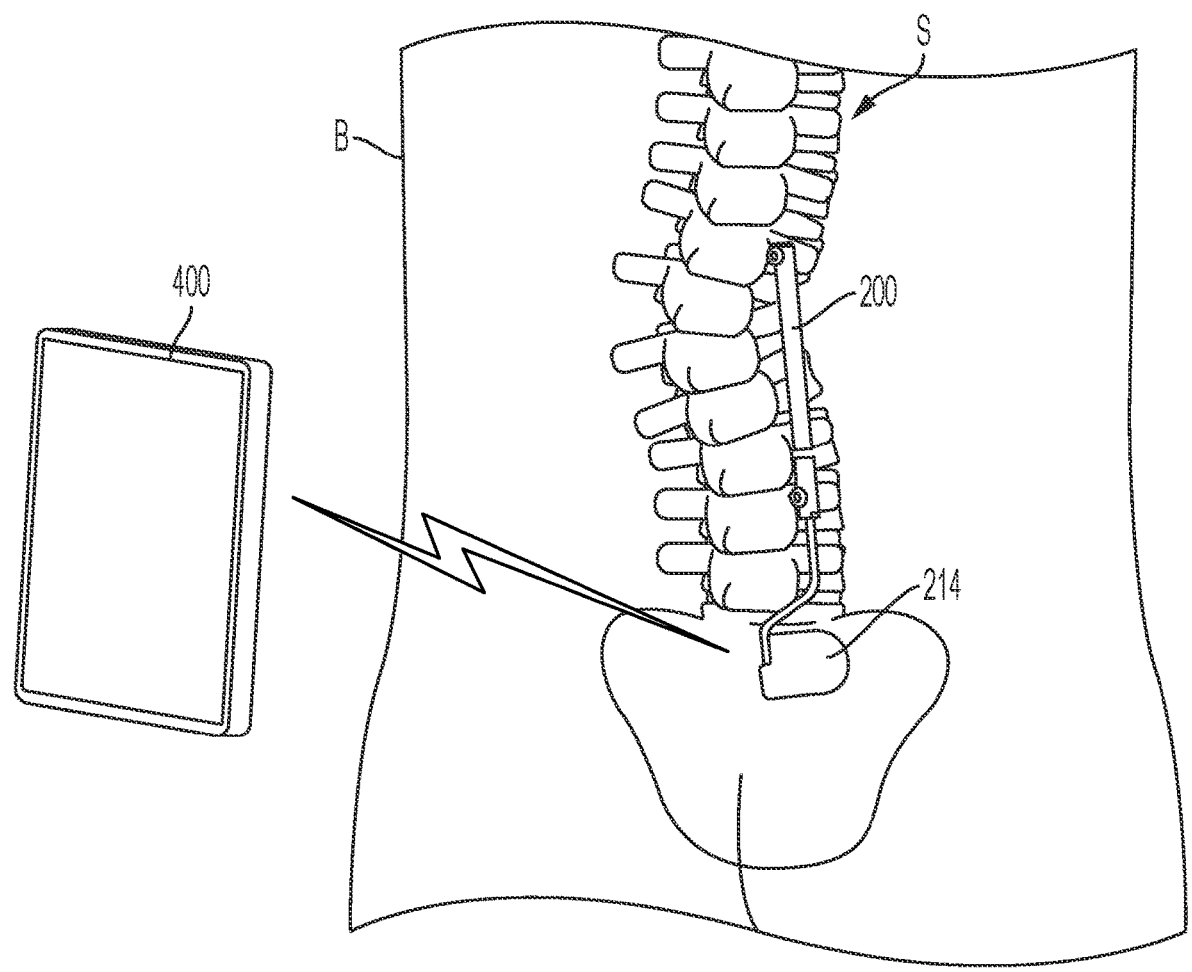
FIG. 42 illustrates a bone lengthening device affixed to a spine of a patient according to one embodiment.

FIG. 42 illustrates bone lengthening device 200 affixed to a spine, referenced as "S", within the body, referenced as "B", of a patient according to one embodiment. An external control and telemetry unit, referenced as 400, is positioned outside the patient body, and functions to control rotation actuator and wirelessly communicate with sensors associated with device 200. The sensors associated with bone lengthening device 200 are preferably integrated in device 200 and can deliver key information to the surgeon relating to device 200 and its environment including: bone lengthening stroke; spine deformity correction (angles, lengths, vectors, etc.); device temperature; regenerated bone stiffness; strain applied on device 200; and, strain applied to the spine "S". One embodiment of the invention includes the ability for the surgeon to update patient protocol by after taking into account the key information data from the device 200 and its environment such scoliotic curve spine and its correction. In practice, the surgeon modifies relevant parameter(s) defined in the software embedded in the telemetry unit 400. The telemetry unit 400 transmits to the actuator device 200 the updated control/command. A remote power unit 214, such as a battery, provides electrical power to device 200. In a preferred embodiment, the control & telemetry unit 400 communicates with the bone lengthening device 200 by wireless communications, such as Bluetooth low energy technology.

Figure 43:
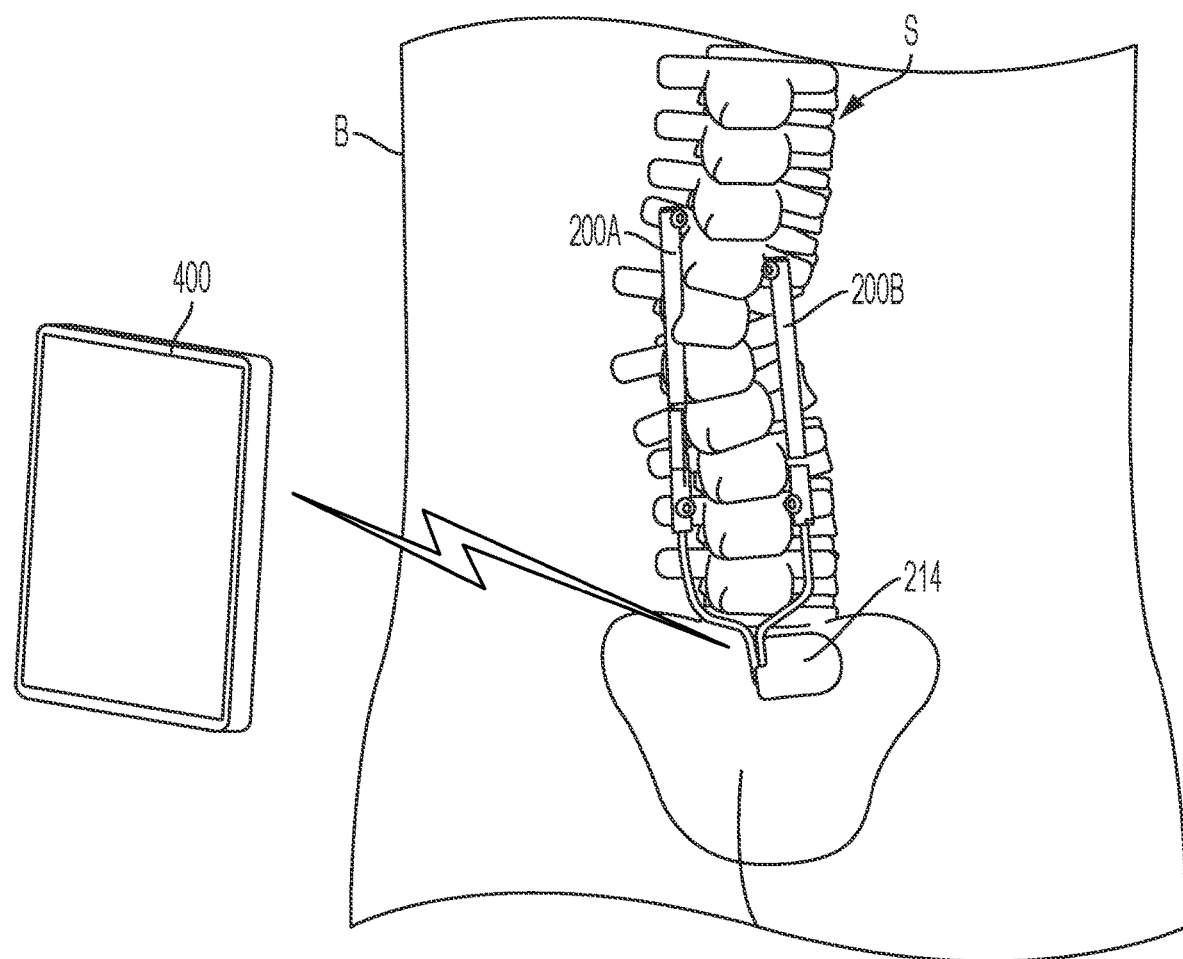
FIG. 43 illustrates a pair of bone lengthening devices affixed to a spine of a patient according to another embodiment.

FIG. 43 illustrates a pair of bone lengthening devices, referenced as 200A and 200B, affixed to a spine "S" of a patient according to another embodiment. As disclosed above, an external control and telemetry unit, referenced as 400, is positioned outside the patient body, and functions to control rotation actuator and wirelessly communicate with sensors associated with device 200. The sensors associated with bone lengthening device 200 are preferably integrated in device 200 and can deliver key information to the surgeon relating to device 200 and its environment including: bone lengthening stroke; spine deformity correction (angles, lengths, vectors, etc.); device temperature; regenerated bone stiffness; strain applied on device 200; and, strain applied to the spine "S". One embodiment of the invention includes the ability for the surgeon to update patient protocol by after taking into account the key information data from the device 200 and its environment such scoliotic curve spine and its correction. In practice, the surgeon modifies relevant parameter(s) defined in the software embedded in the telemetry unit 400. The telemetry unit 400 transmits to the actuator device 200 the updated control/command. A single remote power unit 214, such as a battery, provides electrical power to both devices 200A and 200B. In a preferred embodiment, the control & telemetry unit 400 communicates with the bone lengthening device 200 by wireless communications, such as Bluetooth low energy technology.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

It is to be understood that both the foregoing descriptions are exemplary and explanatory only, and are not restrictive of the methods and devices described herein. In this application, the use of the singular includes the plural unless specifically stated otherwise. All patents, patent applications, publications, and references cited herein are expressly incorporated by reference to the same extent as if each individual publication or patent application was specifically and individually indicated to be incorporated by reference.

What is claimed is:

1. An implant comprising:
   an inner rod having an outer surface;
   an outer rod in telescopic engagement with the inner rod, the outer rod having a threaded inner surface in axial slidable engagement with the outer surface of the inner rod;
   the inner rod and the outer rod each having an end configured for attachment to bone;
   a rotational actuator housed within the inner rod; and
   a lead screw in axial alignment with the rotational actuator and rotationally coupled thereto, the lead screw in threaded engagement with the threaded inner surface of the outer rod,
   whereby rotational motion of the actuator is converted into linear motion, resulting in telescopic changes in the overall axial length of the device.

2. The implant of claim 1, wherein the rotational actuator comprises a non-electric actuator activated by an externally generated magnetic field.

3. The implant of claim 1, wherein the inner rod further includes an externally disposed sleeve extending from an end portion thereof.

4. The implant of claim 1, further comprising:
   a sleeve extending from an end portion of inner rod over the outer rod configured to cover a gap that forms between the end portion and the outer rod as the axial length of the device increases.

5. The implant of claim 1, further comprising:
   a seal disposed adjacent to lead screw between an output shaft of rotational actuator and the inner rod.

6. The implant of claim 1,
   wherein the inner surface of outer rod defines one or more radially inwardly projecting and longitudinally extending channels; and
   wherein the outer surface of the inner rod defines one or more radially outwardly projecting and longitudinally extending lugs that are disposed within the channels.

7. The implant of claim 1, further including an electronics package housed within the inner rod.

8. The implant of claim 7, further including a force sensor configured to detect axial force applied to the device.

9. The implant of claim 7, wherein the rotational actuator comprises an electric motor.

10. The implant of claim 7, further comprising an implantable remote power module in electrical communication with the electronics package via a cable.

11. An implant comprising:
    an inner rod defining an internal volume;
    an outer rod in telescopically adjustable engagement with the inner rod, the outer rod defining an internal cavity bounded by a threaded inner surface;
    the inner rod and the outer rod each having an end configured for attachment to bone;
    an electronics package disposed within the internal volume;
    a rotational actuator in electrical communication with the electronics package;
    the rotational actuator including a motor and a gear assembly;
    a lead screw coupled to the gear assembly, the lead screw having a threaded external surface disposed in threaded engagement with the threaded inner surface of the outer rod; and
    an implantable remote power module in electrical communication with the electronics package via a cable.

12. The implant of claim 11, wherein the outer rod, the inner rod, the rotational actuator, and the lead screw are configured in parallel, and the mechanics thereby translate rotational motion into linear motion.

13. The implant of claim 11, wherein the rotational actuator is disposed between the lead screw and the electronics package.

14. The implant of claim 11, wherein the inner rod further includes an externally disposed sleeve extending from an end portion thereof.

15. The implant of claim 11, further comprising:
    a sleeve extending from an end portion of inner rod over the outer rod configured to cover a gap that forms between the end portion and the outer rod as the axial length of the device increases.

16. The implant of claim 11, further comprising:
    a seal disposed adjacent to lead screw between an output shaft of rotational actuator and the inner rod.

17. The implant of claim 11,
    wherein the inner surface of outer rod defines one or more radially inwardly projecting and longitudinally extending channels; and
    wherein the outer surface of the inner rod defines one or more radially outwardly projecting and longitudinally extending lugs that are disposed within the channels.

18. The implant of claim 11, further comprising:
    a bearing configured to withstand forces applied between the inner rod and the lead screw while allowing rotational movement of the lead screw relative to the inner rod.

19. The implant of claim 11,
wherein the outer rod defines a vent that places an inner cavity of the outer rod in fluid communication with an environment exterior to outer rod.
20. The implant of claim 11, further comprising:
a projecting end portion of the inner rod having an external diameter that is at least as great as the external diameter of the outer rod.

\* \* \* \* \*